US007368267B2

(12) United States Patent
Schmid et al.

(10) Patent No.: US 7,368,267 B2
(45) Date of Patent: May 6, 2008

(54) METHOD FOR THE OXIDATION OF AROMATIC COMPOUNDS

(75) Inventors: Andreas Schmid, Zürich (CH);
Bernhard Witholt, Zürich (CH);
Bruno Bühler, Dortmund (DE);
Bernhard Hauer, Fußgönheim (DE);
Thomas Zelinski, Altrip (DE)

(73) Assignee: BASF Aktiengesellschaft (DE)

( * ) Notice: Subject to any disclaimer, the term of this patent is extended or adjusted under 35 U.S.C. 154(b) by 347 days.

(21) Appl. No.: 10/473,973

(22) PCT Filed: Apr. 5, 2002

(86) PCT No.: PCT/EP02/03803

§ 371 (c)(1),
(2), (4) Date: Oct. 3, 2003

(87) PCT Pub. No.: WO02/081718

PCT Pub. Date: Oct. 17, 2002

(65) Prior Publication Data
US 2004/0106177 A1    Jun. 3, 2004

(30) Foreign Application Priority Data
Apr. 6, 2001    (DE)    ............................. 101 17 359

(51) Int. Cl.
*C12P 7/40*    (2006.01)
*C12P 7/42*    (2006.01)
(52) U.S. Cl. ............... 435/136; 435/147; 435/253.3; 435/253.34
(58) Field of Classification Search .............. 435/136, 435/147, 253.33, 253.34
See application file for complete search history.

(56) References Cited

U.S. PATENT DOCUMENTS 5,017,476 A * 5/1991 Miethe et al. ............... 435/61
5,173,428 A * 12/1992 Witholt et al. ......... 435/252.34

FOREIGN PATENT DOCUMENTS

CA    2 389 138 A1    5/2001

OTHER PUBLICATIONS

CRC Handbook of Chem & Physics 51st Ed 1970-1971, No. b1239 (p. C-174) ,No. a574 (p. C-91) or No. b35 (p. C134).*
Wubbolts, M.G., et al., Biosynthesis of Synthons in Two-Liquid-Phase Media, Biotechnology and Bioengineering, vol. 52, 1996, pp. 301-308.
Wubbolts, M.G., et al., "Efficient production of optically active styrene epoxides in two-liquid phase cultures", Enzyme Microb. Technology, vol. 16, 1994, pp. 887-894.

Panke, S., et al., "Production of enantiopure styrene oxide by recombinant *Escherichia coli* synthesizing a two-component styrene monooxygenase". Biotechnology and Bioengineering, vol. 69, No. 1, 2000, pp. 91-100.
Bühler, B., et al., "Xylene monooxygenase Catalyzes the multistep oxygenation of toluene and pseudocumene to corresponding alcohols, aldehydes, and acids in *Escherichia coli* JM101". Journal of Biological Chemistry, vol. 275, No. 14, 2000, pp. 10085-10092.
Panke, S., et al., "Engineering of a stable whole-cell biocatalyst capable of (S)-styrene oxide formation for continuous two-liquid-phase applications"; Applied and Environmental Microbiology, vol. 65, No. 12, 1999, pp. 5619-5623.
Schmid, A., et al., "Industrial Biocatalysis Today and Tomorrow", Nature, vol. 409, 2001, pp. 258-268.
Harayama, S., et al., "Functional and evolutionary relationships among diverse oxygenases". Ann. Rev. Microbiol., vol. 46, 1992, pp. 565-601.
Harayama, S., et al., "Gene order of the TOL catabolic plasmid upper pathway operon and oxidation of both toluene and benzyl alcohol by the *xylA* product". Journal of Bacteriology, vol. 167, No. 2, 1986, pp. 455-461.
Harayama, S., et al., "Characterization of Five Genes in the Upper—Pathway Operon of TOL Plasmid p WW0 from *Pseudomonas putida* and Identification of the Gene Products", Journal of Bacteriology, vol. 171, No. 9, 1989, pp. 5048-5055.
Legoy, M.D., et al., "Use of Alcohol Dehydrogenase for Flavour Aldehyde Production", Process Biochemistry, vol. 20, 1985, pp. 145-148.
Molinari, F., et al., "Continuous production of isovaleraldehyde through extractive bioconversion in a hollow-fiber membrane bioreactor", Enzyme and Microbial Technology, vol. 20, 1997, pp. 604-611.
Molinari, F., et al., "Biotransformations in two-liquid-phase systems. Production of phenylacetaldehyde by oxidation of 2-phenylethanol with acetic acid bacteria", Enzyme and Microbial Technology, vol. 25, 1999, pp. 729-735.
Molinari, F., et al., "Aldehyde production by alcolhol oxidation with *Gluconobacter oxydans*", Applied Microbiology and Biotechnology, vol. 43, 1995, pp. 989-994.
Ramos, J.L., et al., "Transcriptional Control of the *Pseudomonas* Tol Plasmid Catabolic Operons is Achieved through an Interplay of Host Factors and Plasmid-Encoded Regulators", Annual Reviews in Microbiology, vol. 51, 1997, pp. 341-373.
Riesenberg, D., "High-cell-density cultivation of *Escherichia coli*", Current Opinion in Biotechnology, vol. 2, 1991, pp. 380-384.
Schmid, A., "Der Metabolismus von 2-Hydroxybiphenyl-Verbindungen in *Pseudomonas azelaica* HBP1", Universitat Stuttgart Institut fur Mikrobiologie, 1997, pp. 1-154.
Simmonds, J., et al., Novel biotransformations to produce aromatic and heterocyclic aldehydes, Enzyme and Microbial Technology, vol. 21, 1997, pp. 367-374.
Simmonds, J., et al., "Formation of Benzaldehyde by *Pseudomonas putida* ATCC 12633", vol. 50, 1998, pp. 353-358.

(Continued)

Primary Examiner—Herbert J. Lilling
(74) Attorney, Agent, or Firm—Connolly Bove Lodge & Hutz, LLP

(57) ABSTRACT

The invention relates to a process for the biocatalytic oxidation of aromatic compounds using recombinant xylene monooxygenase-expressing microorganisms in a biphasic reaction medium.

26 Claims, 13 Drawing Sheets

OTHER PUBLICATIONS

Williams, P., et al., "*xylUW*, two genes at the start of the upper pathway operon of TOL plasmid pWW0, appear to play no essential part in determining its catabolic phenotype", Microbiology, vol. 143, 1997, pp. 101-107.

Panke, S., "Production of (*S*)-Styrene Oxide with Recombinant Bacteria", Dissertation submitted to Swiss Federal Institute of Technology Zurich, Switzerland, 1999, pp. 1-208.

* cited by examiner

METHOD FOR THE OXIDATION OF AROMATIC COMPOUNDS

RELATED APPLICATIONS

This application is a national stage application (under 35 U.S.C. 371) of PCT/EP2002/03803 filed Apr. 5, 2002, which claims benefit of German application 101 17 359.8 filed Apr. 6, 2001.

BACKGROUND OF THE INVENTION

Field of the Invention

The invention relates to a process for the biocatalytic oxidation of aromatic compounds.

Aromatic compounds such as aldehydes are important constituents in fragrances and aroma substances (Wittcoff and Reuben 1996). Likewise, they are regarded as starting materials for a variety of polymers, pharmaceuticals and fine chemicals.

The most important chemical synthetic route for preparing a typical aromatic aldehyde, viz. benzaldehyde, starts from toluene (Wittcoff and Reuben 1996). Dichlorination of toluene gives benzylidene chloride, which is hydrolyzed to give benzaldehyde (Scheme 1).

Scheme 1:
Production of benzaldehyde from toluene

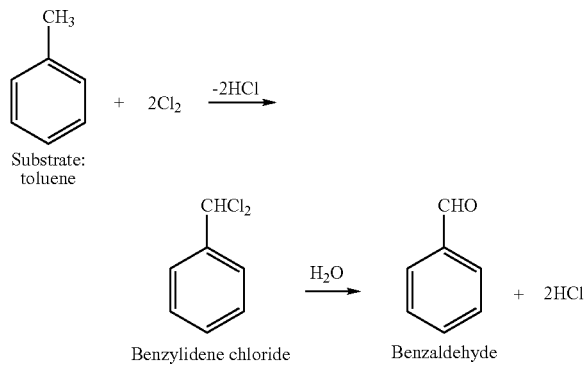

The specific oxidation of only one methyl group or the isolation from product mixtures is the greatest difficulty in chemical synthesis. Moreover, the reactions often have to be carried out with the aid of extremely toxic substances or under extreme reaction conditions. Moreover, the by-products resulting from chemical synthesis cause problems. The production of, for example, 3,4-dimethylbenzaldehyde by chemical synthesis is very difficult owing to the reasons stated above.

An alternative to the above-described chemical synthesis is the biocatalytic production of aromatic compounds such as aldehydes.

The classes of enzymes which are predominantly used for the production of aromatic aldehydes are the transferases, lyases (Simmonds and Robinson 1997; Simmonds and Robinson 1998) and oxidoreductases (Legoy, Kim et al. 1985; Molinari, Villa et al. 1995; Molinari, Aragozzini et al. 1997; Molinari, Gandolfi et al. 1999). The oxidoreductases are of particular interest since they are capable of effecting stereo—and regioselective oxidation of only one methyl group, for example xylenes. Xylenes are regarded as inexpensive substrates and can be converted into the corresponding aldehydes in a two-step reaction.

The TOL plasmid pWWO from *Pseudomonas putida* mt-2 makes possible the catabolism of toluenes and xylenes. The upper and the meta cleavage catabolic pathways are encoded on two separate operons on the plasmid. The enzymes of the upper catabolic pathway catalyze the oxidation of toluenes or xylenes to give the corresponding benzoic acids, and the enzymes of the meta cleavage catabolic pathway catalyze those reactions which cleave benzoic acid into substrates of the citric acid cycle (Harayama, Rekik et al. 1989; Harayama, Kok et al. 1992; Ramos, Marqués et al. 1997; Williams, Shaw et al. 1997). The upper catabolic pathway is of particular interest for the production of aromatic aldehydes. The operon of the upper catabolic pathway contains 5 genes (Harayama, Leppik et al. 1986). As can be seen from Scheme 2, the first enzyme is xylene monooxygenase (XMO), which converts toluenes or xylenes into the corresponding benzyl alcohols.

Scheme 1:
Upper catabolic pathway of *Pseudomonas putida*-mt2

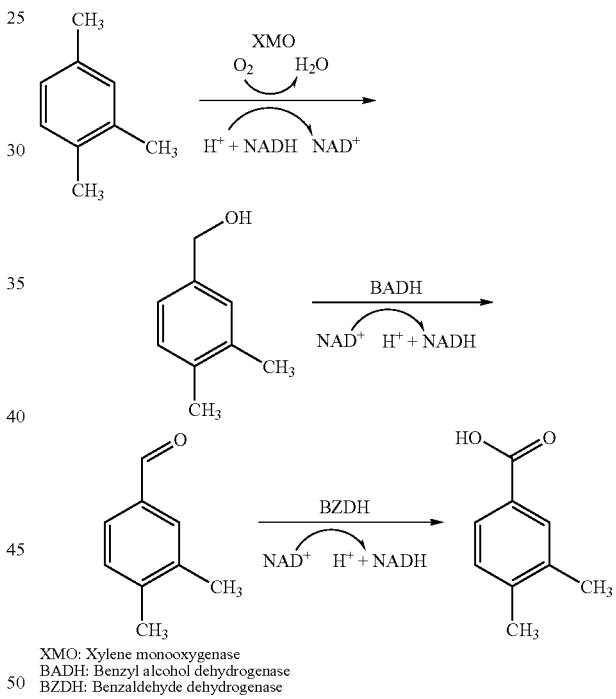

XMO: Xylene monooxygenase
BADH: Benzyl alcohol dehydrogenase
BZDH: Benzaldehyde dehydrogenase The second enzyme is benzyl alcohol dehydrogenase (BADH), which is capable of catalyzing the reaction of benzyl alcohols to benzaldehydes. In the above-described reactions, NADH is consumed by xylene monooxygenase and resynthesized by alcohol dehydrogenase. If these two enzymes were used for the production of benzaldehydes, a balanced NADH balance would result.

When XMO and BADH were used concomitantly in the recombinant *E. coli* for converting toluenes to give the corresponding benzaldehydes, the benzaldehydes were formed in small quantities only. Rather, resynthesis of the benzaldehydes into the corresponding benzyl alcohols was observed (Bühler, Schmid et al. 2000). It has been demonstrated that the equilibrium of the reactions catalyzed by BADH is predominantly toward the alcohols.

According to Bühler, Schmid et al (2000), however, xylene monooxygenase on its own in the absence of BADH is capable of catalyzing the multi-step oxidation of a methyl group of toluenes or xylenes to give benzyl alcohol, benzaldehyde and benzoic acid. This is effected by introducing an oxygen atom of molecular oxygen, that is to say via monooxygenations Bühler, Schmid et al (2000).

Scheme 3 shows the reactions catalyzed by XMO. It must be noted that, in contrast to the dehydrogenation reactions, the monooxygenation reactions are irreversible.

isms. In particular, the novel method is intended to be suitable for being carried out on a larger, semi-industrial or industrial scale.

We have found that this object is achieved by using a biphasic aqueous/organic reaction medium, which we have demonstrated, surprisingly, with the model system of the microbiological oxidation of pseudocumene to give the corresponding oxidation products (alcohol, aldehyde, carboxylic acid). The biphasic system according to the inven-

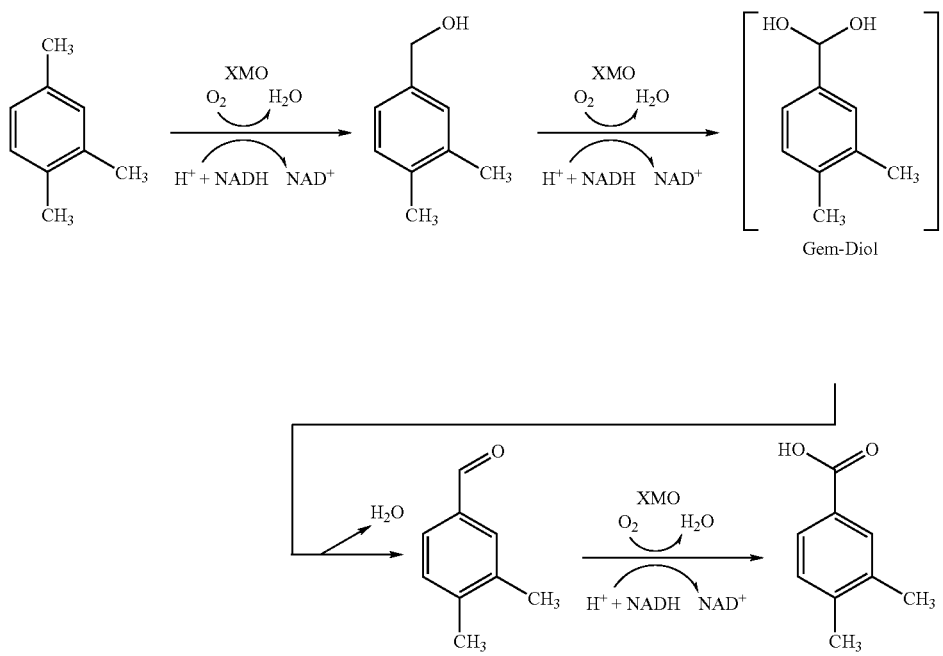

Scheme 3:
Pathways catalyzed by xylene monooxygenase (XMO)

To control the expression of XMO in recombinant *E. coli*, the alk regulation system, which can be induced by n-octane, was used (Panke, Meyer et al. 1999) (see FIG. 1).

The biotechnological production of selectively oxidized aromatics such as 3,4-dimethylbenzaldehyde from inexpensive substrate is of great interest since the regiospecific oxidation of only one methyl group by chemical synthesis is very difficult. The low water solubility and the toxicity of the substrates and the products for the cells are of crucial importance. Thus, toluenes are toxic to *E coli* at a concentration as low as 1-4 mM (Schmid 1997). This limits the applicability of the aqueous monophasic system.

The earlier German Patent Application DE-A-199 51 768.1 describes a method for the biocatalytic production of aromatic aldehydes and/or carboxylic acids in a monophase reaction medium using XMO-expressing microorganisms.

BRIEF DESCRIPTIONS OF THE INVENTION

It is an aim of the present invention to provide an improved biocatalytic process for the oxidation of aromatic compounds with the aid of XMO-producing microorgantion is distinguished over a conventional aqueous monophase system by some important advantages (Table 1).

TABLE 1

| Advantages of multiphasic systems |
|---|
| higher concentrations of substrates/products which are sparingly soluble in water; |
| facilitated working-up of the product by phase separation; |
| reduction of substrate or product inhibitions; |
| shift of the reaction equilibrium toward higher conversion rates by product extraction; |
| reversion of a hydrolytic reaction by reducing the water activity; |
| small reactor volumes and volume flows |
| low risk of microbial contamination |
| low risk of hydrolytic cleavage of unstable substrates or products |

DETAILED DESCRIPTION OF THE INVENTION

In particular, the present invention relates to a process for the biocatalytic oxidation of aromatic compounds which comprises
  a) growing, under aerobic conditions, a microorganism which expresses an enzyme with xylene monooxyge nase (XMO) activity in a biphasic aqueous-organic culture medium comprising an aromatic substrate of the formula II

in which
Ar is an unsubstituted or mono- or polysubstituted mononuclear aromatic ring and
$R^2$ is $—CH=CH_2$, $—(CH_2)_{n+1}R^3$ or $—(CH_2)_nCHO$ where n is an integer from 0 to 15 such as, for example, 0, 1, 2, 3, 4 or 5;
and
$R^3$ is H or OH;

and
b) isolating, from the culture medium, at least one product formed in the XMO-catalyzed oxidation reaction.

In particular, the process according to the invention comprises obtaining the following products of the oxidation reaction:
a) a product of the formula Ia $$Ar—(CH_2)_n—R^1 \quad (Ia)$$

in which
Ar and n have the abovementioned meanings and
$R^1$ is CHO or COOH
when the substrate employed is a compound of the formula II in which
$R^2$ is $—(CH_2)_{n+1}OH$;
b) a product of the above formula Ia or the formula Ib $$Ar—(CH_2)_{n+1}OH \quad (Ib)$$

in which
Ar and n have the abovementioned meanings
when the substrate employed is a compound of the formula II in which
$R^2$ is $—(CH_2)_{n+1}H$;
c) a product of the formula Ic $$Ar—(CH_2)_nCOOH \quad (Ic)$$

in which
Ar has the abovementioned meanings
when the substrate employed is a compound of the formula II in which
$R^2$ is $—(CH_2)_n$ CHO; or
d) a product of the above formula Ia in which $R^1$ is COOH, CHO or $CH_2OH$ and n is 0;

or a compound Ar-epoxy when the substrate employed is a compound of the formula II in which $R^2$ is $—CH=CH_2$.

a) Starting Materials Employed:

The reactions according to the invention can be carried out using the same enzyme (XMO) in one or more steps. The alkylated aromatic compound, the corresponding alcohol or the corresponding aldehyde may be employed as substrate. The desired degree of oxidation of the substrate employed can be controlled as will be illustrated in greater detail hereinbelow.

The aromatic ring system Ar in the compounds of the formula I and II which are prepared in accordance with the invention or employed as substrates can be mono- or polysubstituted. The position of the ring substituent(s) can be selected as desired. However, the meta and/or para position relative to the side chain to be oxidized is preferred.

Suitable substituents on the aromatic compound comprise $C_1$-$C_4$-alkyl such as methyl, ethyl, n- and i-propyl and n-butyl, in particular methyl and ethyl, $C_1$-$C_4$-alkoxy, in particular methoxy and ethoxy, halogen such as F, Cl, Br and I, in particular Cl and nitro.

Specific nonlimiting examples of substrates of the formula II which can be oxidized by XMO in the method according to the invention are toluene, xylenes, styrene, m- and/or p-methyl, ethyl-, methoxy-, nitro- and chloro-substituted toluenes, and m-bromo-substituted toluene and pseudocumene (i.e. trimethylbenzenes); and the corresponding alcohols or aldehydes of these compounds.

b) Organic Phase

The choice of the organic phase is important for the biphasic system used in accordance with the invention and depends on a variety of parameters:
the toxic or inhibitory effect of the organic phase on the cells
the solubility of the substrates and products in the organic phase
the partition coefficients of substrate and product
flammability and toxicity of the organic phase
difference in density of the organic phase and water
the boiling point of the organic phase Preferably used in accordance with the invention as the organic phase of the biphasic reaction medium is an apolar organic compound which has a partition coefficient of $>10^4$ in a biphasic n-octanol/water system.

Also preferred is the use of those organic phases which have a boiling point or boiling range at 1 atm which exceeds the boiling point of the oxidation product(s) by approximately 50 to 200° C., in particular of the oxidation product to be isolated with the highest boiling point. An organic phase which is especially preferably used is di($C_5$-$C_{12}$-alkyl) phthalate or a mixture of such phthalates. Especially preferably used are dioctyl phthalate (bisethyl hexyl phthalate) and those which can simultaneously act as antifoams during the fermentation.

In a preferred variant of the process according to the invention, the reaction product is obtained by separating off the organic phase and removing the oxidation product(s) dissolved therein by distillation.

c) Expression Constructs and Biocatalyst Employed

The processes according to the invention are preferably carried out using XMO, encoded by the genes xylA and xylB according to xylMA GENBANK-Accession No. M37480 and corresponding isoenzymes. XMO originates preferably from bacteria of the genus *Pseudomonas*, in particular the species *Pseudomonas putida*, preferably strain mt-2 (ATCC 33015).

The invention also encompasses the use of "functional equivalents" of the XMOs which are disclosed specifically.

"Functional equivalents" or analogs of the specifically disclosed monooxygenases are, for the purposes of the present invention, enzymes which differ from them but continue to show the desired reaction and are useful for the preparation of alcohols, aldehydes and/or carboxylic acids of the above formula I.

"Functional equivalents" are understood as meaning in accordance with the invention in particular enzyme mutants which in at least one sequence position have an amino acid other than the original amino acid, but which still catalyze one of the abovementioned oxidation reactions. Thus, "functional equivalents" encompass the mutants obtainable by one or more amino acid additions, substitutions, deletions and/or inversions, it being possible for the abovementioned modifications to occur in any sequence position as long as they give rise to a mutant with the catalytic activity according to the invention. Functional equivalence exists also in particular when the reactivity patterns between mutant and unmodified enzyme agree in terms of quality, i.e. when, for example, identical substrates are converted at different rates.

Naturally, "functional equivalents" also encompass monooxygenases which are accessible from other organisms, for example other bacteria than those mentioned specifically herein, and naturally occurring variants or isoenzymes. For example, regions of homologous sequences can be identified by sequence alignment, and equivalent enzymes can be determined in accordance with the specific tasks of the invention.

Also encompassed in accordance with the invention is the use of other nucleic acid sequences (simplex and duplex DNA and RNA sequences) other than those mentioned specifically, which encode one of the above monooxygenases and their functional equivalents. Further nucleic acid sequences which are useful in accordance with the invention thus differ from the specifically employed sequences by addition, substitution, insertion or deletion of one or more nucleotides, but continue to encode a monooxygenase with the desired range of characteristics.

Also encompassed in accordance with the invention is the use of those nucleic acid sequences which comprise what are known as silent mutations or which are modified in comparison with a specifically mentioned sequence in accordance with the codon usage of a specific source organism or host organism, as are naturally occurring variants such as, for example, splice variants thereof. The invention also relates to sequences which can be obtained by conservative nucleotide substitutions (i.e. the amino acid in question is replaced by an amino acid of the same charge, size, polarity and/or solubility).

The coding XMO sequence is a component of expression constructs comprising, under the genetic control of regulatory nucleic acid sequences, a nucleic acid sequence encoding a monooxygenase enzyme which can be used in accordance with the invention. Such constructs according to the invention preferably comprise a promoter 5'-upstream of the coding sequence in question and a terminator sequence 3'-downstream and, if appropriate, further customary regulatory elements, in each case linked operably to the coding sequence. "Operable linkage" is understood as meaning the sequential arrangement of promoter, coding sequence, terminator and, if appropriate, further regulatory elements in such a way that each of the regulatory elements can fulfill its function in the expression of the coding sequence. Examples of sequences which can be linked operably are targeting sequences and translation enhancers, other enhancers, polyadenylation signals and the like. Further regulatory elements comprise selectable markers, amplification signals, origins of replication and the like.

The natural regulatory sequence may still be present before the actual structural gene, in addition to the artificial regulatory sequences. If appropriate, this natural regulation can be eliminated by genetic modification, and gene expression can be increased or reduced. However, the gene construct can also be simple in structure, that is to say no additional regulatory signals are inserted before the structural gene, and the natural promoter together with its regulation is not removed. Instead, the natural regulatory sequence is mutated in such a way that regulation no longer takes place and that gene expression is increased or reduced. One or more copies of the nucleic acid sequences may be present in the gene construct.

Examples of useful promoters are: cos, tac, trp, tet, trp-tet, lpp, lac, lpp-lac, lacIq, T7, T5, T3, gal, trc, ara, SP6, I-PR or I-PL promoter, which are used advantageously in Gram-negative bacteria, and the Gram-positive promoters amy and SPO2, the yeast promoters ADC1, MFa, AC, P-60, CYC1, GAPDH or the plant promoters CaMV/35S, SSU, OCS, lib4, usp, STLS1, B33, not or the ubiquitine or phaseolin promoter. The use of inducible promoters, such as, for example, light- or temperature-inducible promoters, such as the $P_rP_l$-promoter, is especially preferred.

In principle, all natural promoters together with their regulatory sequences may be used. Additionally, synthetic promoters may also be used advantageously.

The abovementioned regulatory sequences are intended to make possible the controlled expression of the nucleic acid sequences. Depending on the host organism, this may mean, for example, that the gene is expressed or overexpressed after induction only, or that it is expressed and/or overexpressed immediately.

The regulatory sequences or factors can preferably have a positive effect on expression, thus increasing or reducing it. Thus, the regulatory elements can advantageously be enhanced at the transcriptional level by using strong transcription signals such as promoters and/or enhancers. Besides, an enhancement of translation is also possible, for example by improving the stability of the mRNA.

An expression cassette according to the invention is generated by fusing a suitable promoter to a suitable monooxygenase nucleotide sequence and a terminator or polyadenylation signal. To do so, customary recombination and cloning techniques are used as are described, for example, in Sambrook et al.

For expression in a suitable host organism, the recombinant nucleic acid construct or gene construct is advantageously inserted into a host-specific vector which makes possible the optimal expression of the genes in the host. Vectors are well known to the skilled worker and can be found, for example, in "Cloning Vectors" (Pouwels P. H. et al.).

In addition to plasmids, vectors are also understood as meaning all the other vectors known to the skilled worker such as, for example, phages, viruses such as SV40, CMV, CaMV, baculovirus and adenovirus, transposons, IS elements, phasmids, cosmids, and linear or circular DNA. These vectors can be replicated autonomously in the host organism or else replicated chromosomally.

Such vectors according to the invention can assist in the generation of recombinant microorganisms which are transformed for example with at least one vector according to the invention and which can be employed in the process according to the invention. The above-described recombinant constructs according to the invention are advantageously introduced into, and expressed in, a suitable host system. It is preferred to use cloning and transfection methods with which the skilled worker is familiar, such as, for example, coprecipitation, protoplast fusion, electroporation, retroviral transfection and the like, in order to express the abovementioned nucleic acids in the expression system in question. Suitable systems are described, for example, in Current Protocols in Molecular Biology, F. Ausubel et al.

d) Microorganisms

Host organisms which are suitable are, in principle, all organisms which make possible the expression of the nucleic acids according to the invention, of their allelic variants, of their functional equivalents or their derivatives, and which can be employed for carrying out the microbiological oxidation reaction according to the invention. Host organisms are understood as meaning, for example, bacteria, fungi, yeasts, plant cells or animal cells. Preferred organisms are bacteria.

However, an XMO-expressing microorganism which is preferably used is one which has essentially no benzyl alcohol dehydrogenase (BADH) activity and/or no benzaldehyde dehydrogenase (BZDH) activity. A microorganism transformed with the expression plasmid pSPZ3 is especially preferably used.

The microorganisms which are preferably used in accordance with the invention are bacteria of the genus *Escherichia*, in particular *E. coli*, such as, for example, strain JM101.

The transformation of microorganisms with a vector is carried out in accordance with the invention using established standard techniques and therefore does not require a more detailed description.

Selection of successfully transformed organisms can be effected by marker genes which are also present in the vector or in the expression cassette. Examples of such marker genes are genes for resistance to antibiotics and genes for enzymes which catalyze a color reaction which brings about staining of the transformed cell. These cells can then be selected by means of automatic cell sorting. Microorganisms successfully transformed with a vector which carry a suitable gene for resistance to antibiotics (for example G418 or hygromycin) can be selected by suitable liquid or solid media comprising antibiotics. Marker proteins which are presented at the cell surface can be used for selection by affinity chromatography.

The combination of the host organisms and the vectors which match the organisms, such as plasmids, viruses or phages, such as, for example, plasmids with the RNA polymerase/promoter system, phages λ or μ or other temperent phages or transposons and/or further advantageous regulatory sequences forms an expression system.

In accordance with an especially preferred embodiment, a recombinant microorganism is used which is transformed with an expression vector which carries the XMO-encoding genes xylM and xylA, for example under the genetic control of the alk regulatory system from *Pseudomonas* oleovorans GPo1.

The microorganism is especially preferably transformed with the xylMA-encoding expression plasmid pSPZ3.

The alk regulatory system from *Pseudomonas* oleovorans GPo1 is known per se. The expression of the first of the two alk gene clusters mentioned above is under the control of alkBp, the alk-promoter, and starts in the presence of the functional regulatory protein alkS, which is encoded by the second alk gene cluster, and in the presence of an inductor such as, for example, an alkane, for example n-octane, or a compound which is not closely related to these, such as, for example, dicyclopropyl ketone (DCPK) (8, 22, 23). The use of the alk regulatory system in *E. coli* has the advantage that catabolite repression does not take place.

e) Carrying Out the Process

The process according to the invention can be carried out batchwise, semibatchwise or continuously in conventional bioreactors. Making use of a semi-batch process is especially preferred. Here, the culture medium, with the exception of a small residue such as, for example, approximately 1 to 5% by volume, is removed from the reactor after the conversion has ended. This residue then acts as inoculum for the batch which follows.

The optimal process parameter concentration such as aeration rate and oxygen input, concentration of starting materials, pH, temperature, composition of the reaction medium with regard to organic phase and nutrient medium, feed time and feed rate and the like can be selected by the skilled worker without undue effort taking into consideration the disclosure in the experimental part which follows. Thus, for example, the pH of the reaction medium can be used as a parameter for the productivity of the biocatalyst.

n-Octane is preferably used as inductor in the method according to the invention, especially preferably in an amount of from 0.001 to 0.5% (v/v).

In a further preferred process variant, the conversion according to the invention is carried out in essentially antibiotic-free reaction media. Surprisingly, this is advantageous since, under the prevailing reaction conditions, it would indeed have been expected that the recombinant microorganism used loses the plasmid which has been introduced. Dispensing with antibiotics in the reaction medium, which is made possible in accordance with the invention, means significant financial savings since the use of antibiotics can be dispensed with and, moreover, no residual antibiotics have to be removed from the processed reaction medium.

The degree of oxidation of the substrates employed in accordance with the invention can be controlled in various ways. For example, samples are taken from the culture medium at regular intervals and the content of the corresponding alcohol, aldehyde and/or carboxylic acid derivatives is studied by gas chromatography alone, gas chromatography coupled to mass spectrometry (GC-MS) or high-performance liquid chromatography. Depending on which oxidized derivative is desired, or when a desired mixing ratio has established, the incubation is terminated. This can be effected for example by killing the microorganisms or by removing them from the culture medium, for example by centrifugation and decanting and/or by treatment with acid, for example trichloroacetic acid, or by heat treatment.

The oxidized aromatic compound can then be isolated from the culture medium in particular the organic phase, with the aid of customary separation methods, for example by simple distillation, fractional distillation, rectification, if appropriate in vacuo, or by applying suitable chromatographic methods, but preferably by distillation.

f) Preparation of 3,4-dimethylbenzaldehyde:

In a preferred embodiment of the invention, bis(2-ethylhexyl) phthalate (dioctyl phthalate) was chosen as the organic phase in accordance with the above criteria for the organic phase for the oxidation according to the invention of aromatic compounds and in particular for the preparation of 3,4-dimethylbenzaldehyde from pseudocumene in a biphasic fed batch process. Both substrate and product dissolve readily in dioctyl phthalate. Moreover, this inexpensive organic substance is highly flame retardant and constitutes a nontoxic second phase for *E. coli*. The high boiling point of dioctyl phthalate (380° C. under atmospheric pressure) permits the separation of the products by distillation.

The distribution coefficients of pseudocumene, 3,4-dimethylbenzyl alcohol, 3,4-dimethylbenzaldehyde and 3,4-dimethylbenzoic acid between dioctyl phthalate and M9 medium as the aqueous phase can be seen from Table 2.

TABLE 2

Partition coefficients in DOP/M9 (glucose) biphasic system

| Substance | Partition coefficient |
| --- | --- |
| Pseudocumene | 24300 ± 1500 |
| 3,4-Dimethylbenzyl alcohol | 50 ± 3 |
| 3,4-Dimethylbenzaldehyde | 906 ± 20 |
| 3,4-Dimethylbenzoic acid | 0.188 ± 0.005 |

The kinetics of this multistep process play a decisive role in the biphasic fed batch process preferred in accordance with the invention for the preparation of 3,4-dimethylbenzaldehyde by means of recombinant XMO-expressing *E. coli*. Thus, it has been observed that 3,4-dimethylbenzoic acid (DBA) is formed only when the concentration of the remaining substrate is quite low (<90 mM in the organic phase; corresponds to approximately 3.7 µM in the aqueous phase). A factor which probably also contributes to this phenomenon, in addition to the higher affinity of xylene monooxygenase for pseudocumene than for the corresponding aldehyde, is noncompetitive inhibition of the third oxidiation step by pseudocumene. Also, when the pseudocumene concentrations in the organic phase were above 150 mM (which corresponds to approximately 6.2 µM in the aqueous phase), a simultaneous formation of 3,4-dimethylbenzyl alcohol and 3,4-dimethylbenzaldehyde was observed. At a pseudocumene concentration of less than 150 mM, however, the predominant product is 3,4-dimethylbenzaldehyde. The formation of 3,4-dimethylbenzoic acid is also inhibited when the concentration of the alcohol in the aqueous phase exceeds the concentration of the aldehyde.

When recombinant *E. coli* lack XMO activity, the backward reaction of 3,4-dimethylbenzaldehyde to 3,4-dimethylbenzyl alcohol was observed. This can be attributed to unspecific alcohol dehydrogenase activities in the *E. coli* strain used. In this reaction too, the equilibrium is towards the alcohol (Bühler, Schmid et al. 2000), as was the case with BADH.

The enzyme activity also depends on the glucose concentration in the medium. Thus, not only high glucose concentrations in the medium, but also glucose limitation and oxygen limitation, have an inhibitory effect on enzyme activity.

In accordance with a preferred embodiment of the invention, which is described in greater detail in the examples which follow, 3,4-dimethylbenzaldehyde was produced in a kinetically controlled multistep reaction from pseudocumene using *E. coli* in which the genes of the *Pseudomonas putida* mt-2 xylene monooxygenase were employed recombinantly. This is made possible by the ability of xylene monooxygenase of catalyzing the oxidation of the xylenes to the corresponding acids via the corresponding alcohols and aldehydes. The kinetics of this multistep reaction were used to specifically concentrate the aldehyde. Using a biphasic fed batch process in which the starting material is added via an organic phase, 484 ml (96.5%) of 3,4-dimethylbenzaldehyde were produced from a 30 liter batch on a pilot scale and were isolated by centrifugation and distillation.

Moreover, the culture medium used for the conversion has been successfully optimized further in accordance with the invention and process-relevant parameters have been determined and optimized successfully in accordance with the invention. Also, it was demonstrated that the plasmid and the XMO genes remain stable over 60 hours and 14 generations without selection pressure.

Starting from the above results for the conversion of pseudocumene, the skilled worker can apply the general teaching of the invention to the biocatalytic conversion of further starting materials of the above formula I without undue burden, if appropriate using other microorganisms. Factors which will be considered in this context are, in particular, modifications with regard to the composition of the reaction medium (for example buffers, nutrients, organic phase) and the process conditions (for example substrate concentration, operating conditions, reactor type, aeration, reaction time), working-up of the reaction mixture and the like.

The invention is now illustrated in greater detail with reference to the following nonlimiting use examples and with reference to the appended Figures.

FIG. 1 shows: plasmid pSZP3 regulated by the alk regulatory system; alkBp, promoter of the alk operon; alkS, gene for the positive regulator AlkS; xylM* and xylA, genes encoding xylene monooxygenase (* means that an NdeI interface had been removed in xylM); Km kanamycin resistance gene; T4t, transcriptional terminator of phage T4.

FIG. 2 shows: the cell dry weight (CDW), the glucose concentration and the acetic acid concentration in the fermentation with feed solution I with yeast extract FIG. 3 shows: the concentration of pseudocumene, 3,4-dimethylbenzyl alcohol, 3,4-dimethylbenzaldehyde, 3,4-dimethylbenzoic acid and octane in the aqueous and organic phase in the fermentation with feed solution I with yeast extract FIG. 4 shows: a) cell dry weight, glucose concentration and acetic acid concentration in the fermentation with feed solution I without yeast extract;
  b) concentrations of pseudocumene, 3,4-dimethylbenzyl alcohol, 3,4-dimethylbenzaldehyde, 3,4-dimethylbenzoic acid and octane in the aqueous and organic phase in the fermentation with feed solution I without yeast extract FIG. 5 shows: the cell dry weight, the glucose concentration and the acetic acid concentration in the fermentation with increased substrate concentration FIG. 6 shows: the concentrations of pseudocumene, 3,4-dimethylbenzyl alcohol, 3,4-dimethylbenzaldehyde, 3,4-dimethylbenzoic acid and octane in the aqueous and organic phase in the fermentation with increased substrate concentration; the arrow indicates the simultaneous reduction in the feed and aeration rates FIG. 7 shows: the cell dry weight (CDW), the glucose concentration and the acetic acid concentration when the growth curve of *E. coli* JM101 in Riesenberg medium is recorded FIG. 8 shows: the cell dry weight, the glucose concentration and the acetic acid concentration in the fermentation with high cell density when starting the fed batch culture FIG. 9 shows: the concentrations of pseudocumene, 3,4-dimethylbenzyl alcohol, 3,4-dimethylbenzaidehyde, 3,4-dimethylbenzoic acid and octane in the aqueous and organic phase in the fermentation with high cell density at the beginning of the fed batch culture; the arrow indicates the addition of 1% (v/v) pseudocumene FIG. 10 shows: the cell dry weight, the glucose concentration and the acetic acid concentration in the fermentation with normal cell density at the beginning of the fed-batch culture FIG. 11 shows: the concentrations of pseudocumene, 3,4-dimethylbenzyl alcohol, 3,4-dimethylbenzaldehyde, 3,4-dimethylbenzoic acid and octane in the aqueous and organic phase in the fermentation with normal cell density at the beginning of the fed-batch culture FIG. 12 shows: the cell dry weight, the glycerol concentration and the acetic acid concentration in the fermentation with glycerol as carbon source FIG. 13 shows: the concentrations of pseudocumene, 3,4-dimethylbenzyl alcohol, 3,4-dimethylbenzaldehyde, 3,4-dimethylbenzoic acid and octane in the aqueous and organic phase in the fermentation with glycerol as carbon source.

FIG. 14 shows: the cell dry weight, the glycerol concentration and the acetic acid concentration in the fermentation with glycerol as carbon source and a higher substrate concentration FIG. 15 shows: the concentrations of pseudocumene, 3,4-dimethylbenzyl alcohol, 3,4-dimethylbenzaldehyde, 3,4-dimethylbenzoic acid and octane in the aqueous and organic phase in the fermentation with glycerol as carbon source and higher pseudocumene concentration FIG. 16 shows: the cell dry weight, the glucose concentration and the acetic acid concentration in the repetitive fed-batch culture, day 1

ABBREVATIONS USED

| CDW | cell dry weight |
| DBAlk | 3,4-dimethylbenzyl alcohol |
| DBAld | 3,4-dimethylbenzaldehyde |
| DBA | 3,4-dimethylbenzoic acid |
| DOP | dioctyl phthalate |

-continued

| $NAD^+$ | β-nicotinamide adenine dinucleotide, oxidized form |
| NADH | β-nicotinamide adenine dinucleotide, reduced form |
| P | pseudocumene (trimethylbenzene) |
| ppm | parts per million |
| rpm | rotations per minute |
| v/v | volume by volume |
| w/v | weight by volume |
| XMO | xylene monooxygenase |

MATERIALS AND METHODS

1. Apparatuses
a) Analytical equipment

| GC Fisons Instruments | HRCG Mega 2 Series Machery-Nagel, Önsingen, (CH) Column: Silicone capillary column OPTIMA-5 (25 m; internal diameter 0.32 mm, film thickness 0.25 μm) |
| GC | HP 5890 Series 2 GC Plus Column: capillary column CARBOWAX 20 M 25 m * 0.25 mm * 0.25 mm (Macherey-Nagel) |
| Spectrophotometer | Novaspec II Pharmacia LKB | b) Equipment for the biotransformation

| 3 liter stirred reactor | Case, RU Groningen, (NL) |
| 42 liter stirred reactor | New MBR, Zürich (CH) Control: pH, temperature, stirring rate Operating system: OS/9 Data recording: Caroline II (PCS, Wetzikon CH) | c) Down-stream apparatuses

| Centrifuge | Cryofuge 8000 Heraeus Christ, Zürich (CH) |
| Vacuum pump | Type D8B Leybold-Heraeus, Zürich (CH) |
| Cooling apparatus | 2219 Multitemp II Thermomatic Circulator LKB Broma Multitemp II |
| Vacuum gauge | TypeTR 216 Leybold Bakuum GmbH, Cologne (Germany) |

2. Chemicals
The chemicals used for the experiments were analytical grade. To determine the glucose, glycerol and acetic acid concentrations, the following enzyme assay kits were used and employed in accordance with the manufacturers' instructions (Sigma Diagnostics, Boehringer Mannheim):

| Glucose kit | Sigma Diagnostics | Glucose (Method 315) |
| Glycerol UV assay | Boehringer Mannheim | Glycerol (Art. No. 148270) |
| Acetic acid UV assay | Boehringer Mannheim | Acetic acid (Art. No. 148 261) |
| Glucose UV assay | Boehringer Mannheim | Lactose/D-glucose (Art. No. 986 119) |

Figure 1:
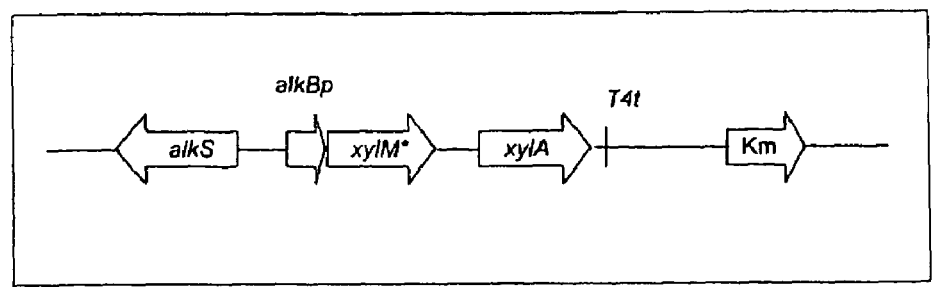

3. Biological material
a) Bacteria
The following bacterial strain was used for the experiments according to the invention:
E. coli JM101 F, [traD26 proAB$^+$ lacII$^q$, Δ(lacZ)M15] pro AB/supE, thi-1, Δ(lac-proAB) (Sambrook, Fritsch et al. 1989)

b) Plasmid
The following plasmid was used for the experiments according to the invention (FIG. 1): pSPZ3 alkS, AlkBp, xylMA, ori pMB1; Km$^r$ (Panke 1999)

4. Media and solutions
a) Trace element solution US* (Panke, 1999)

per liter:
1 M hydrochloric acid
1.5 g $MnCl_2*4H_2O$
1.05 g $ZnSO_4$
0.3 g $H_3BO_3$
0.25 g $Na_2MoO_4*2H_2O$
0.15 g $CuCl_2*2H_2O$
0.84 g $Na_2EDTA*2H_2O$

| MATERIALS AND METHODS | | |
|---|---|---|
| | 4.12 g CaCl$_2$*H$_2$O | |
| | 4.87 g FeSO$_4$*7H$_2$O | |
| (when using Riesenberg medium: 8.87 g FeSO$_4$*7H$_2$O) | | |
| b) LB medium (Luria Bertani medium) | | |
| per liter: | 10 g tryptone | |
| | 5 g yeast extract | |
| | 5 g NaCl | |
| c) M9* medium | | |
| per liter: | 25.5 g Na$_2$HPO$_4$*2H$_2$O | |
| | 9 g KH$_2$PO$_4$ | |
| | 1 g NH$_4$Cl | |
| | 1 g NaCl | |
| The pH was brought to 7.4 with NaOH | | |
| Supplemented with: | 0.5% (w/v) glucose | |
| | 2 ml MgSO$_4$ (1 M) | |
| | 1 ml thiamine (1% w/v) | |
| | 1 ml kanamycin (50 mg/ml) | |
| | 1 ml trace element solution US* | |
| d) M9 medium: | | |
| per liter: | 8.82 g KH$_2$PO$_4$ | |
| | 10.85 g K$_2$HPO$_4$ | |
| | 8.82 g Na$_2$HPO$_4$ | |
| | 11.06 g Na$_2$HPO$_4$*2H$_2$O | |
| | 1 g NH$_4$Cl | |
| | 0.5 g NaCl | |
| The pH was brought to 7.1 with NaOH | | |
| Supplemented with: | 0.5% (v/v) glucose | |
| | 2 ml MgSO$_4$ (1 M) | |
| | 1 ml thiamine (1% w/v) | |
| | 1 ml kanamycin (50 mg/ml) | |
| | 1 ml trace element solution | |
| e) Riesenberg medium: | | |
| per liter: | 13.3 g KH$_2$PO$_4$ | |
| | 4.0 g (NH$_4$)$_2$HPO$_4$ | |
| | 1.7 g citric acid | |
| The pH was brought to 6.8 with NH$_4$OH and to 7.1 with NaOH | | |
| Supplemented with: | 0.7-2.5% (v/v) glucose | |
| | or 0.7% (v/v) glycerol | |
| | 5 ml MgSO$_4$ (1 M) | |
| | 1 ml kanamycin (50 mg/ml) | |
| | 1 ml thiamine (1% w/v) | |
| | 5 ml-10 ml trace element solution | |
| The media and the magnesium sulfate and glucose stock solutions were autoclaved. | | |
| The kanamycin and thiamine stock solutions were filter-sterilized. | | |
| f) Feed solution I for M9 medium: | | |
| per liter | 45% (w/v) glucose | |
| | 9 g MgSO$_4$*7H$_2$O | |
| | (50 g yeast extract) | |
| The pH was brought to 3 with HCl. Yeast extract was not used in all of the experiments. | | |
| g) Feed solution II for Riesenberg medium: | | |
| per liter | 73% (w/v) glucose | |
| | 19.6 g MgSO$_4$*7H$_2$O | |
| The feed solution was filtered-sterilized | | |
| h) Organic phase for the conversion of pseudocumene: | | |
| per liter of dioctyl phthalate | 20-48.0 ml pseudocumene | |
| | 10 ml octane | |
| i) Solution 1 | | |
| per 100 ml | 333 µl 3 M NaAc pH 5.8 | |
| | 2 ml 2.5 M MnCl$_2$ | |
| | 100 µl 5 M NaCl | |
| k) Solution 2 | | |
| per 50 ml | 167 µl 3 M NaAc pH 5.8 | |
| | 8.3 ml 30% (w/v) glycerol | |
| | 3.5 ml 1 M CaCl$_2$ | |
| | 200 µl 2.5 M MnCl$_2$ | |
| 5. Molecular biological methods | | |
| 5.1 Competent cells | | |
| A shake flask containing 50 ml of LB medium was inoculated with 500 µl of preculture and incubated overnight. After an OD$_{450}$ of 0.4 had been reached, the culture liquid was distributed into SS34 tubes (40 M) and centrifuged for 8 minutes at 8000 rpm at 4° C. The supernatant was discarded. The cells were resuspended in 8 ml of the above solution 1 and incubated on ice for 20 minutes. Then, the cells were separated from solution 1 by centrifugation for 8 minutes at 8000 rpm. They were subsequently resuspended in 800 µl of the above solution 2 on ice, and divided between Eppendorf tubes in 100 µl aliquots. They were stored at −80° C. | | |
| 5.2 Plasmid isolation | | |
| The plasmid was isolated using the E.Z.N.A. ® Plasmid Miniprep Kit I (peQLab Biotechnologie GmbH). 20 ml of LB medium comprising 1% (w/v) glucose and 20 µl of kanamycin (50 mg/ml) were inoculated with a colony of transformed *E. coli* JM101 and incubated overnight at 37° C. After the incubation, the culture liquid was divided into 4 15 ml tubes and centrifuged. The following process steps were carried out as specified in the protocol of the Miniprep Kit I. The amount of the plasmid obtained was estimated by gel electrophoresis. | | |
| 5.3 Cell transformation | | |
| *E. coli* JM101 was transformed with the plasmid pSPZ3 by heat shock. 100 µl of frozen competent cells were defrosted for 20 minutes on ice. After addition of 3 µl of plasmid, the cells were incubated on ice for 10-20 minutes. Then, they were subjected to a heat shock at 37° C. for 3 minutes and, after the time had elapsed, immediately returned to ice for 5-10 minutes. After addition of 1 ml of LB medium, the cells were incubated for 1 hour at 37° C. Finally, the cells were plated onto LB agar plates, comprising 20 µl of kanamycin (50 mg/ml) and incubated overnight at 37° C. | | |
| 6. Laboratory-scale biotransformations | | |
| The stirred reactor used for the biotransformation accommodates a volume of 3 liters. Temperature, pH and stirring rate could be adjusted automatically. The oxygen dissolved in the medium (DOT) was measured by means of an oxygen electrode and plotted thus as time. | | |
| 6.1 Precultures | | |
| Preculture 1: 4 ml of LB medium comprising 1% (w/v) glucose and 4 µl of kanamycin (50 mg/ml) were inoculated with a colony of freshly transformed *E. coli* JM101 (pSPZ3) and incubated overnight at 30° C. with shaking. | | |
| Preculture 2: Preculture 1 was added to 100 ml of M9* medium comprising 0.5% (w/v) glucose or glycerol, 200 µl of magnesium sulfate (1 M), 100 µl of trace element solution US*, 100 µl of thiamine (1% w/v) and 100 µl of kanamycin (50 mg/ml), and the mixture was incubated at 30° C. for 10-12 hours with shaking. | | |
| 6.2 Batch | | |
| 900 ml of medium (M9 or Riesenberg medium) which had been sterilized together with the bioreactor and supplemented with thiamine, trace elements, glucose or glycerol, magnesium sulfate and, where stated, with antibiotics were inoculated with 100 ml of preculture. The stirring rate was 1500 rpm. Also, the temperature was adjusted to 30° C. and the pH to 7.1 by addition of 25% NH$_4$OH and 25% phosphoric acid. The aeration rate was 1 l/min. | | |
| 6.3 Fed batch | | |
| After consumption of the added glucose and the utilization of the acetic acid produced by the bacterial metabolism (approx. 9-12 hours), a glucose/- or glycerol/magnesium sulfate solution to which yeast extract had been added in some cases was added to the medium. The glucose feed rate varied between 4.5 g/h and 11.25 g/h in the different experiments. Also, 4 ml of thiamine stock solution and 4 ml of the trace element solution US* were added. | | |
| 6.4 Biotransformation | | |
| One hour after starting the fed-batch culture, the organic phase (comprising 10 ml of n-octane as inductor and 20-40 ml of pseudocumene) was added. At the same time, the stirring rate was increased to 2000 rpm. When oxygen limitation of the bacteria was observed (DOT < 10%), the air supply was increased to 1.7 liters/minute. If required, the stirring rate was increased to 2500 rpm. The biotransformation was carried out for approx. 15-30 hours. After the beginning of the fed-batch culture, samples were taken periodically and analyzed. | | |
| 7. Pilot-scale biotransformation | | |
| The above-described 42 liter stirred reactor was employed for carrying out the biotransformation on a pilot scale. Stirring rate, temperature, pH and pressure in the reactor | | |

Figure 7:
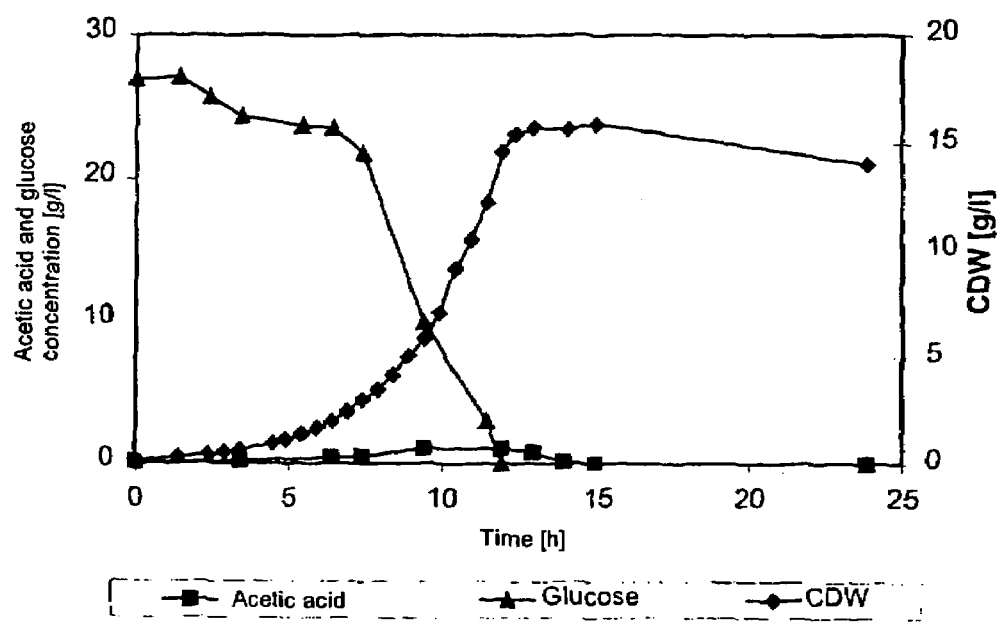

| MATERIALS AND METHODS |
|---|
| were controlled automatically. The reactor was controlled automatically by the OS/9 operating system using the program Caroline II (PCS, Wetzikon, Switzerland). |
| 7.1 Precultures<br>Preculture 1: 4 ml of LB medium comprising 1% (w/v) glucose and 4 μl of kanamycin (50 mg/ml) were inoculated with a colony of freshly transformed E. coli JM101 (pSPZ3) and incubated at 30° C. overnight with shaking.<br>Preculture 2: Preculture 1 was incubated in 100 ml during 10-12 hours at 30° C. with shaking.<br>Preculture 3: Preculture 2 was added to 2 l of M9* medium comprising 0.5% (w/v) glucose or glycerol, 200 μl of magnesium sulfate (1 M), 100 μl of trace element solution US*, 100 μl of thiamine (1% w/v) and 100 μl of kanamycin (50 mg/ml). |
| 7.2 Batch<br>14 liters of Riesenberg medium were sterilized in a reactor. After the sterilization, the medium was supplemented with trace elements, magnesium sulfate, thiamine and 0.7% (w/v) glucose. The addition of kanamycin was dispensed with. The stirred reactor was inoculated with 1-1.5 liters of preculture. The stirring rate was 400-600 rpm. The aeration rate was 20 l/min. |
| 7.3 Fed-batch culture<br>After consumption of the glucose added and of the acetic acid produced by the bacteria, feed solution II was fed. The feed rate was 180 g/h at the beginning, but was increased when glucose was limited. Moreover, 60 ml of thiamine (1% w/v), 60 ml of trace element solution US* and 15 ml of n-octane for cell induction were added. |
| 7.4 Biotransformation<br>After 1 hour, 15 liters of dioctyl phthalate comprising 4.3% (v/v) of pseudocumene and 1% (v/v) of n-octane were added as organic phase. The stirring rate was increased to 1000 rpm. Likewise, the aeration rate was increased to 40 l/min. Samples were taken periodically and analyzed for their substrate, product, byproduct and octane contents. Likewise, the cell dry weight, the glucose concentration and the acetic acid concentration were determined. FIG. 7 shows the course of the process in the form of a diagram. |
| 8. Determination of the partition coefficients in the biphasic system.<br>The partition coefficient is defined as the concentration of the substance in the organic phase relative to the concentration of the substance in the aqueous phase. To determine the partition coefficients of Riesenberg medium with glycerol and dioctyl phthalate, various concentrations of pseudocumene, 3,4-dimethylbenzyl alcohol, 3,4-dimethylbenzaldehyde and 3,4-dimethylbenzoic acid were added to 1:1 mixtures of dioctyl phthalate and Riesenberg medium. The partition equilibrium was established by vigorous shaking and incubation overnight. Aqueous and organic phases were separated by centrifugation. The organic phases were diluted with ether and the aqueous phase was extracted and analyzed by GC. The concentrations in the 2 phases were determined on the basis of the measurements, and the partition coefficients were calculated. In each case the determination was carried out in triplicate. |
| 9. Sample analyses |
| 9.1 GC analysis<br>The aqueous phase and the organic phase were separated by centrifugation at 20° C. Ice-cold ether with 0.1 mM dodecane was then added to the samples as internal standard. After addition of a saturating concentration of sodium chloride, the aqueous phase was extracted by vigorous shaking for 1 minute, and the phases were subsequently separated by centrifugation. The organic phase is dried by addition of sodium sulfate and analyzed. The substrate, product, by-product and octane contents were determined by GC (Nagel, Oensingen, Switzerland). The samples were injected without splitting. Hydrogen was used as the carrier gas. The following temperature program was employed for the measurement: 2 minutes at 40° C.; from 40 to 70° C. at a heating rate of 15° C./min; from 70 to 105° C. at a heating rate of 5° C./min and from 105° C. to 280° C. at a heating rate of 20° C./min; 5 min at 280° C. The chemical compounds were measured using a flame-ionization detector. The data of substrate, product and by-products were represented in a diagram. Likewise, the specific activity and the aldehyde formation rate were represented in a diagram. To this end, the following calculations were carried out:<br>Specific activity = unit/g cell dry weight<br>One unit is the activity produced by 1 μmol of total product (DBAlk, DBAld, DBAcid) in 1 minute.<br>Aldehyde formation rate = 1 μmol of aldehyde formed per minute/g cell dry weight |
| 9.2 Determination of the optical density<br>The cells were separated by centrifugation at 4° C. The volume of the aqueous phase was recorded on the tube, and the supernatant was subsequently drawn off and discarded. The cell pellet was taken up in a medium volume equivalent to the aqueous phase and resuspended therein. The optical density was measured at 450 nm with the aid of a spectrophotometer. |
| 9.3 Determination of the glucose, glycerol and acetic acid concentration<br>a) The glucose, glycerol and acetic acid concentrations in the aqueous phase were determined with the aid of the above enzyme assay kits.<br>b) Determination of the acetic acid concentration by GC 50 μl of aqueous phase were treated with 350 μl of water, 50 μl of $H_3PO_4$ (85%) and 50 μl of 100 mM sodium butyrate as internal standard. The latter was analyzed using an HP 5890 Series 2 GC. The temperature program used was as follows: 0.5 min at 85° C., from 85-100° C. at a heating rate of 12° C./min, from 110-200° C. at a heating rate of 79° C./min, 2.5 min at 200° C. Helium was used as the carrier gas. |
| 9.4 Determination of the plasmid stability<br>The samples were centrifuged, and the intermediate phase of the aqueous and the organic phases was marked on the tube. The supernatant was discarded, and the cell pellet was resuspended in a volume of medium which was equivalent to the aqueous phase. The sample was diluted and the dilution was plated onto LB agar plates, LB agar plates with 20 μl of kanamycin (50 mg/ml) and LB agar plates with 20 μl of kanamycin (50 mg/ml) and 20 μl of indole. If the cells express the XMO genes, the colonies on the LB indole agar plates turn blue. This can be explained by the fact that the XMO genes catalyze the oxidation of indole to indigo. The plates were incubated overnight at 30° C. and then counted. The live microbial counts were compared. |
| 10. Work-up (down-stream processing) |
| 10.1 Centrifugation<br>After the reactor contents had been harvested, the organic phase and the aqueous phase were separated for 15 minutes at 5000 rpm and 4° C. using a Heraeus centrifuge. The aqueous phase was discarded, while the organic phase was dried with sodium sulfate (1 kg/15 l organic phase) and stored at 5° C. The sodium sulfate was removed before the distillation step (using paper filters). |
| 10.2 Distillation<br>The organic phase in the flask was heated to 200° C. under a medium vacuum of between 0.08 mbar and 0.15 mbar. The distillate was divided into three fractions, viz. into first runnings (110° C.-125° C.), a main fraction (120° C.-170° C.) and tailings (170° C.-200° C.). The vacuum and the temperature were controlled automatically. |

I. Laboratory-Scale Pseudocumene Biotransformation Experiments

The laboratory-scale biotransformations (Examples 1, 2 and 3) were intended firstly to determine and optimize the process-relevant parameters and secondly to optimize the medium. The aim was to increase the amount of 3,4-dimethylbenzaldehyde (DBAld) produced during the biotransformation.

Moreover, the formation of acetic acid, which is produced by the cells as metabolite was released into the medium, was studied in the biotransformations. When this metabolite is present at an unduly high concentration, it inhibits biomass growth. The use of a new medium (Riesenberg medium) was intended to achieve higher cell density and thus a higher enzyme activity per volume. The variation of the feed solution also counts as a measure for optimizing the medium. Biotransformations in which the feed solution was not supplemented with yeast extract were carried out, since the latter contains, inter alia, undefined constituents which make difficult the reproducibility of the biotransformation. The effect of the two carbon sources glucose and glycerol on enzyme activity and acetic acid production was also tested.

The stability of the plasmid and of the XMO genes without selection pressure was additionally studied. Thus, biotransformations without kanamycin were carried out.

A biphasic-fed batch process was tested for the production of DBAld. Here, the fed batch was started after a batch, followed by addition of the organic phase comprising the substrate and the inductor. The figures show the results obtained from the beginning of the fed-batch culture. In diagrams which show the substrate, product, by-product and octane concentrations, the concentrations of the substances in the aqueous and organic phases were added together. The specific activity is defined as 1 μmol of total product formed (DBAlk, DBAld and DBAcid) per minute per g of cell dry weight. The aldehyde formation rate corresponds to 1 μmol of 3,4-dimethylbenzaldehyde formed per minute per g of cell dry weight.

EXAMPLE 1

Biotransformations With M9 Medium

Experiment 1.1: Fermentation With Feed Solution I With Yeast Extract

The biotransformation was carried out using the above-described fermentation process. Before the inoculation, the medium was supplemented with 0.5% (w/v) glucose. After the batch, the biomass reached a cell dry weight of 3.1 g/l. The feed rate was 10 g/h at the beginning of the fed-batch culture, corresponding to a glucose feed rate of 4.5 g/h. To prevent unduly severe glucose limitation, the feed rate was increased stepwise. The aeration rate was increased from 1 l/min to 1.7 l/min after 3 hours to circumvent oxygen limitation.

Figure 2:
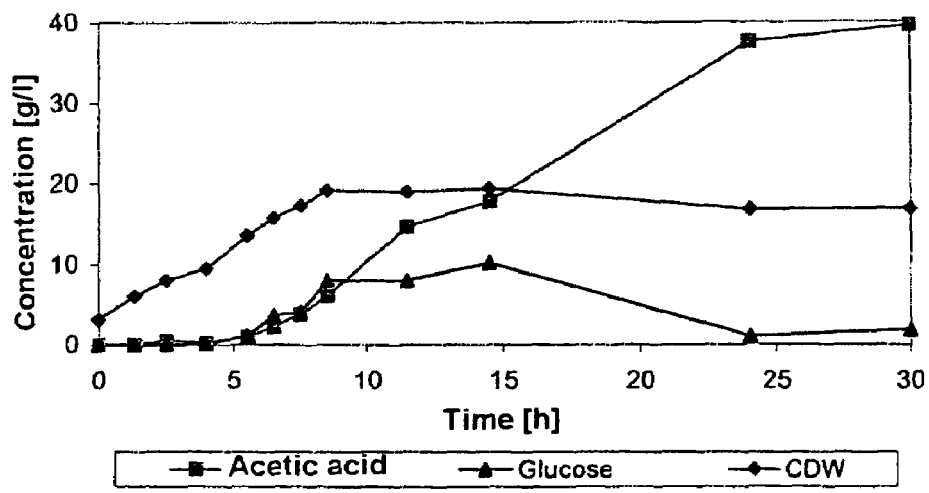

FIG. 2 shows the data of the acetic acid and glucose concentrations and of the cell dry weight. After reaching the stationary phase, the cell dry weight was 19 g/l. When the bacterial growth stopped after 8 hours, the acetic acid concentration was 10 g/l, while the glucose concentration was 9 g/l.

Figure 3:
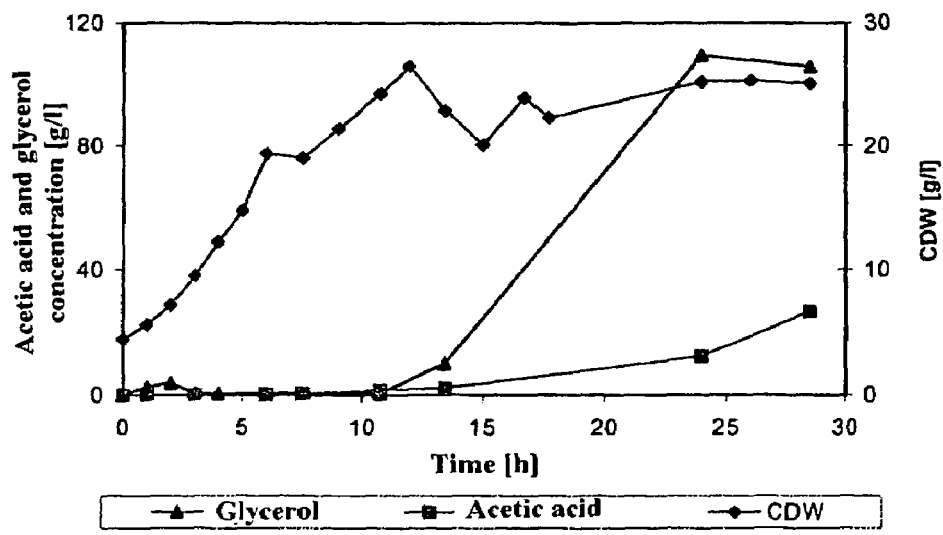

FIG. 3 shows the changes in the pseudocumene, 3,4-dimethylbenzaldehyde (DBAlk), 3,4 dimethylbenzyl alcohol (DBAlk), 3,4-dimethylbenzoic acid (DBAcid) and octane concentrations. When the organic phase was added, the pseudocumene concentration was 1.6% (v/v). After a 1.5 hour induction phase, 3,4-dimethylbenzaldehyde was produced predominantly. When a substrate concentration of 90 mM was reached, the formation of DBAcid started. After 10 hours, an acid concentration of 22 mM was reached and remained constant for the remainder of the biotransformation. DBAlk was only produced after 10 hours. At the end of the biotransformation after 30 hours, the DBAld concentration was 43 mM and the DBAlk concentration 20 mM.

The specific activity and the aldehyde formation rate reached maxima of 12.6 U/g CDW and 9.8 U/g CDW, respectively, after 4 hours. Thereafter, the specific activity decreased continuously. However, the aldehyde formation rate only dropped steeply 5.5 hours after the beginning of the fed-batch culture; this corresponded to the point in time at which the formation of 3,4-dimethylbenzoic acid started. After 8 hours, the aldehyde formation rate started to climb again.

With reference to the results obtained, it can be confirmed that the formation of 3,4-dimethylbenzoic acid starts at a pseudocumene concentration of 90 mM.

Experiment 1.2: Fermentation With Feed Solution I Without Yeast Extract

The purpose of this fermentation was to study the effects of feed solution I without yeast extract on the biotransformation.

Figure 4A:
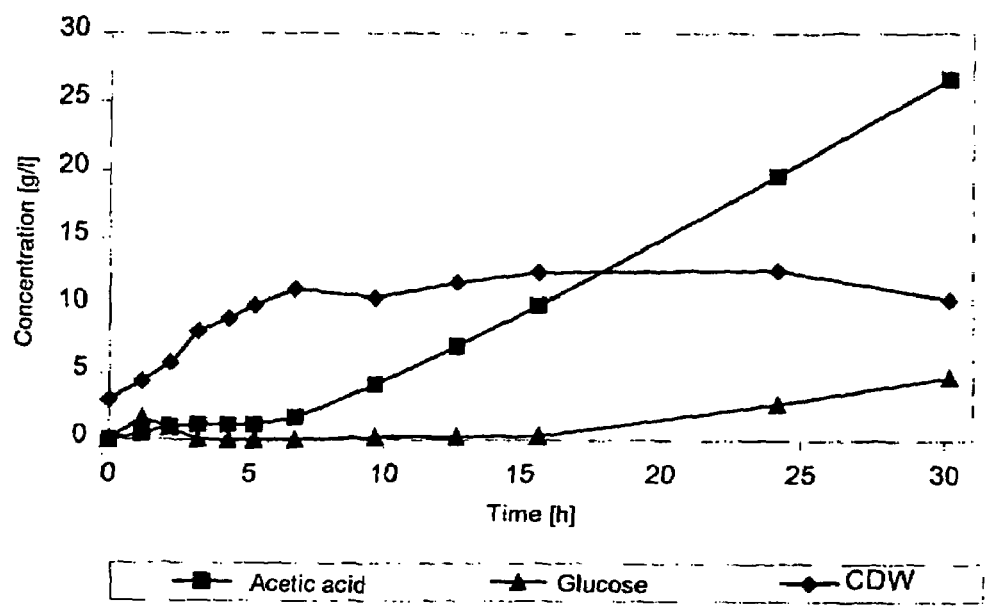

FIG. 4a shows the courses of the glucose and acetic acid concentrations and of the cell dry weight. Prior to inoculation, the glucose concentration in the medium amounted to 0.5% (w/v). At the beginning of the fed-batch culture, the cell dry weight concentration was 3 g/l. The feed solution without yeast extract was fed at a constant rate of 10 g/h. This corresponds to a glucose feed rate of 4.5 g/h. After 7 hours, the stirring rate was increased from 2000 rpm to 2500 rpm to circumvent oxygen limitation (DOT>10%).

Even low glucose concentrations resulted in the formation of acetic acid. Thus, the acetic acid concentration was kept constant at a value of 1 g/l by glucose limitation. When the glucose concentration in the medium was increased, the acetic acid concentration increased continuously up to 26.6 g/l zu. At the end of the biotransformation, the biomass concentration amounted to 12 g/l.

Figure 4B:
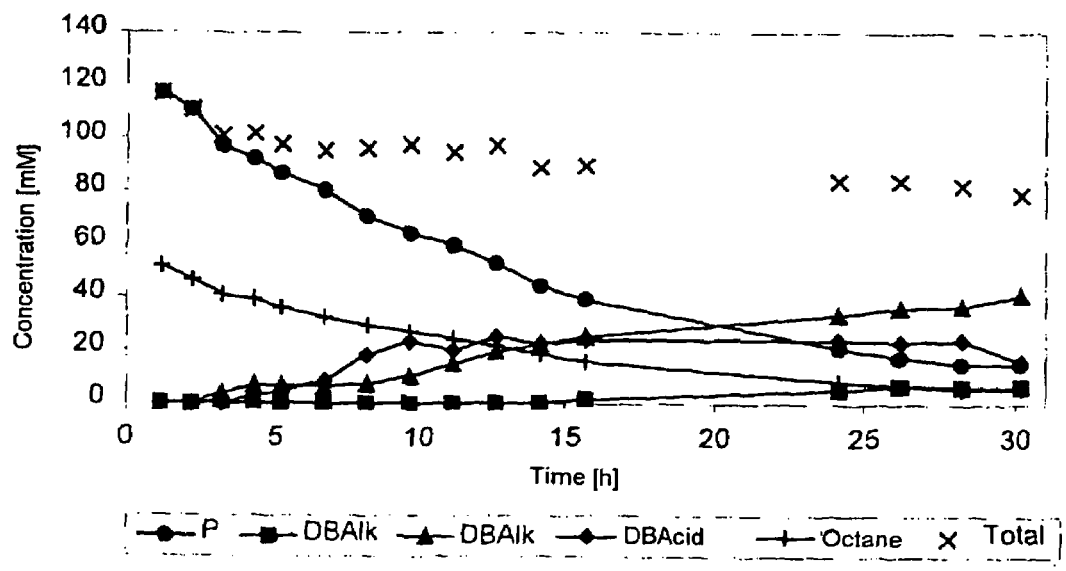

The substrate concentration in the organic phase amounted to 1.6% (v/v) (FIG. 4b). 2 hours after addition of the organic phase, the formation of 3,4-dimethylbenzaldehyde started. From a substrate concentration of 90 mM, however, DBAcid was produced predominantly, while the 3,4-dimethylbenzaldehyde concentration remained constant. The formation of DBAld started again only after 10 hours had elapsed and reached a concentration of 41 mM. When the enzyme activity was lower in the second part of the biotransformation (from 15 hours onwards), DBAlk was produced. 3 hours after the beginning of the fed-batch culture, the specific activity reached a maximum of 10 U/g CDW, but dropped thereafter. After a minor increase, the specific activity decreased continuously 9 hours after the beginning of the fed batch culture. The aldehyde formation rate too reaches a maximum of 7.1 U/g CDW after 3 hours. As in the experiment described before, a drop in the aldehyde formation rate was observed at the beginning of the 3,4-dimethylbenzoic acid formation.

This fermentation shows that omission of the yeast extract has an important effect on biomass growth and enzyme activity. Thus, a lower concentration of cell dry matter was achieved during the fed-batch culture than in the preceding preliminary experiment. Likewise, a lower specific activity and aldehyde formation rate were observed. In comparison with the preceding experiment, a slower decrease in the specific activity was observed. Likewise, the acetic acid concentrations in the medium were lower than in the preceding experiment.

Experiment 1.3: Fermentation With Increased Substrate Concentration

It has been found in earlier experiments that an increase in the substrate concentration has a positive effect on the formation of 3,4-dimethylbenzaldehyde. Thus, the substrate concentration was increased from 1.6% (v/v) to 3.1% (v/v). Furthermore, it was attempted to keep the glucose concentration, and thus also the acetic acid concentration in the medium, down. In the $2^{nd}$ part of the biotransformation, 15 hours after the beginning of the fed batch culture, the effect of a simultaneously occurring severe glucose and oxygen limitation was studied. Thus, the feed supply and the aeration were reduced simultaneously.

Figure 5:
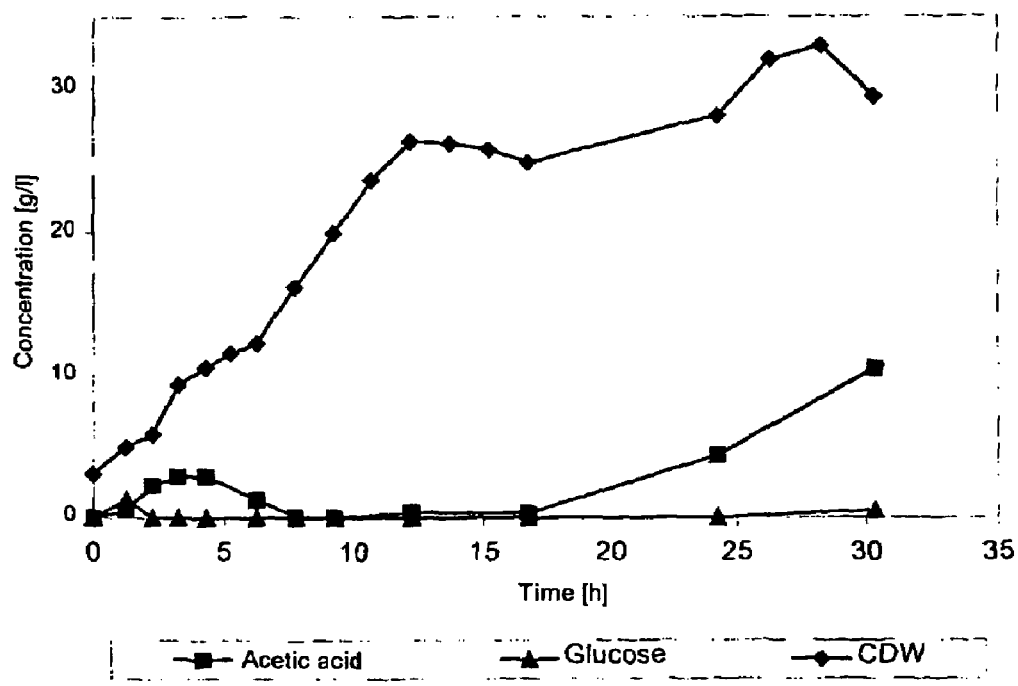

0.5% (w/v) of glucose was added to the medium prior to inoculation. Starting from a cell dry weight of 3 g/l, the biomass increased during the fed batch up to a concentration of 27 g/l. At the beginning of the fed batch culture, feed solution with yeast extract was fed at a rate of 10 g/h (glucose feed rate 4.5 g/h). The feed rate was subsequently increased stepwise, however, glucose limitation was retained in order to prevent a high acetic acid concentration in the medium. It was possible to keep down the acetic acid concentration in the medium over a prolonged period. This even resulted in utilization of the acetic acid (FIG. 5). To prevent oxygen limitation, the aeration rate was increased from 1 l/min to 1.5 l/min and the stirrer speed from 2000 rpm to 2500 rpm. After 16 hours, the feed rate and the aeration rate were reduced simultaneously, which resulted in severe glucose and oxygen limitation and in an increase in the acetic acid concentration.

Figure 6:
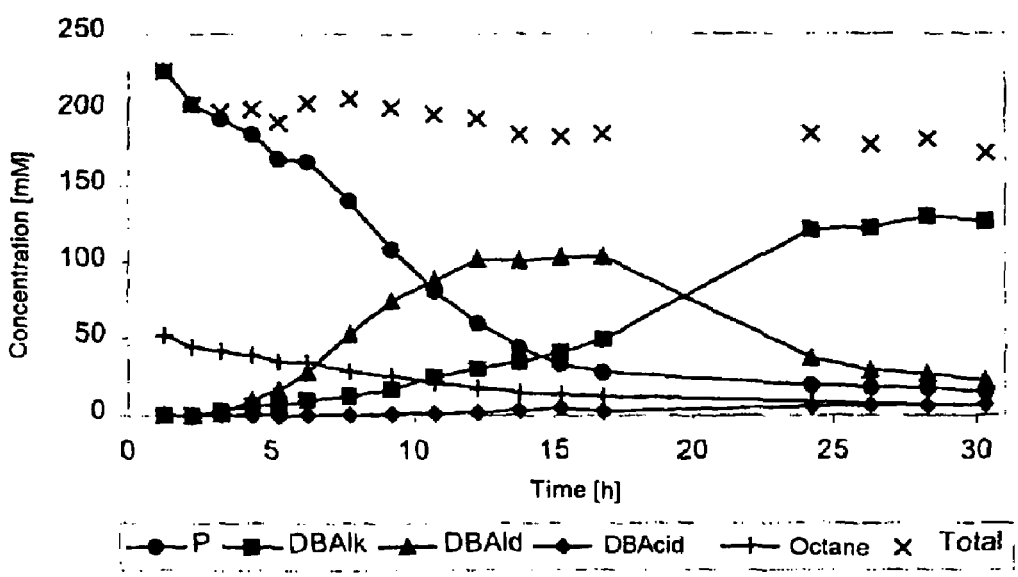

The biotransformation was started with a substrate concentration of 3.1% (v/v). 1 hour after induction of the cells, the formation of 3,4-dimethylbenzaldehyde (BDAld) and 3,4-dimethylbenzyl alcohol (DBAlk) commenced. 16 hours after starting the fed-batch culture and after reducing the feed rate and the aeration rate, a backconversion of DBAld into DBAlk by unspecific *E. coli* alcohol dehydrogenases was observed (FIG. 6). After 30 hours, the DBAlk concentration amounted to 130 mM, while the DBAld concentration was only 30 mM. A minor production of 3,4-dimethylbenzoic acid was observed during the biotransformation.

After the maximum of the specific activity of 18.6 U/g CDW had been reached 8 hours after starting the fed-batch culture, the specific activity dropped. This can be attributed firstly to the cells' growth stop at this point in time and secondly to the decrease in the substrate concentration. The aldehyde formation rate reached a maximum of 16 U/g CDW. In contrast to the fermentation with feed solution I with yeast extract and the fermentation in which the feed solution I had not been supplemented by yeast extract, no drop in activity was observed after 5 hours.

The fermentation which was carried out has demonstrated that higher substrate concentrations result in higher enzyme activity. Since it was possible to keep down the formation of acetic acid during the biotransformation, a higher cell density was achieved during the fed-batch culture. Owing to the results obtained, it can be said that a simultaneously occurring glucose and oxygen limitation results in a loss in the xylene monooxygenase activity. The unspecific *E. coli* alcohol dehydrogenases converted 3,4-dimethylbenzaldehyde back to 3,4-dimethylbenzyl alcohol.

EXAMPLE 2

Biotransformation With the Riesenberg Medium

To obtain a higher cell density, and thus a higher activity per volume, a new medium termed high-cell density medium in the literature was used (Riesenberg 1991). In contrast to the M9 medium which had been used to date, the Riesenberg medium contains smaller quantities of phosphate salts. Moreover, the medium contains more nitrogen since aqueous ammonia is used for adjusting the pH. The feed solution II which was used together with the Riesenberg medium contains no yeast extract, in contrast to feed solution I.

Experiment 2.1: Growth Curve of *E. Coli* JM101 (PSZP3) With Riesenberg Medium

To study the growth behavior of *E. Coli* JM101(pSZP3) and the formation of the metabolite acetic acid when using Riesenberg medium, a growth curve was first recorded. The stability of the plasmid and of the XMO genes was checked using indole agar plates and kanamycin agar plates. Thus, it was possible to test whether the plasmid was passed down into subsequent generations and expressed.

The batch medium contained 2.5% (w/v) of glucose. The batch culture took 15 hours, with degradation of the acetic acid produced (FIG. 7). After the inoculation, the cell dry weight amounted to 0.18 g/l, and it increased up to 15 g/l at a growth rate of 0.4 $h^{-1}$. 1 g/l of acetic acid was produced during the batch culture.

The growth behavior of the cells when using Riesenberg medium was similar as in the case with M9 medium. A minor formation of acetic acid was observed during the batch culture. Also, the period within which the acetic acid was reutilized by the bacteria was relatively short.

With reference to the numbers of colonies on the LB agar plates, the LB agar plates with kanamycin and the LB agar plates with indole and kanamycin, it can be said that the plasmid and the XMO genes remained stable. Thus, no significant difference was found between the colonies grown on various LB agar plates. Likewise, the color reaction on the LB agar plates with indole was positive.

Experiment 2.2: High Cell Density Fermentation at the Beginning of the Fed-Batch Culture After the growth curve had been recorded, Riesenberg medium was employed in the biotransformation. This was done with particular emphasis on biomass growth and in this context also the formation of acetic acid.

The aim of the fermentation was to achieve a higher biomass concentration at the end of the biotransformation by starting the fed-batch culture with a high initial cell density. This would lead to an increase in the activity per volume during the biotransformation.

Figure 8:
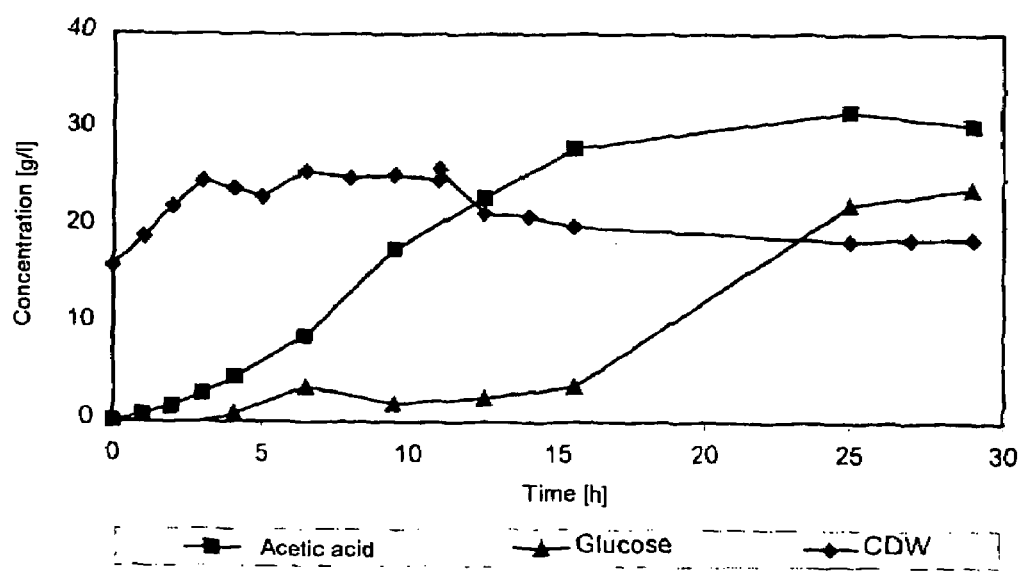

To achieve a relatively high cell density after the batch, the medium was supplemented with 2.5% (w/v) instead of 0.5% (w/v) of glucose. At the beginning of the fed-batch culture, the cell dry weight amounted to 16 g/l (FIG. 8). During the fed-batch culture, the biomass did not continue to increase greatly and reached a maximum concentration of 24.7 g/l.

During the fed-batch culture, the bioreactor was constantly supplied with 12.5 g/h feed solution II. This corresponds to a glucose feed rate of 9 g/h. Since the cells were subjected to oxygen limitation after as little as 2 hours and the stirring rate and the aeration rate had already been set to the maximum, the reactor was aerated with oxygen instead of air. By doing so, it was possible to keep the oxygen dissolved in the medium (DOT) above a value of 10%. From hour 5 onward, the cells were no longer subject to glucose limitation. The glucose concentration remained constant at 2 g/l between hour 5 after the beginning of the fed-batch culture and hour 15, but increased thereafter up to 25 g/l. Since the glucose concentration in the medium was relatively high, the acetic acid concentration in the medium went up continuously and reached a value of 30 g/l at the end of the fed-batch culture.

At the beginning of the fed-batch culture, the medium was supplemented with 1 liter of organic phase with a substrate concentration of 3.4% (v/v).

Figure 9:
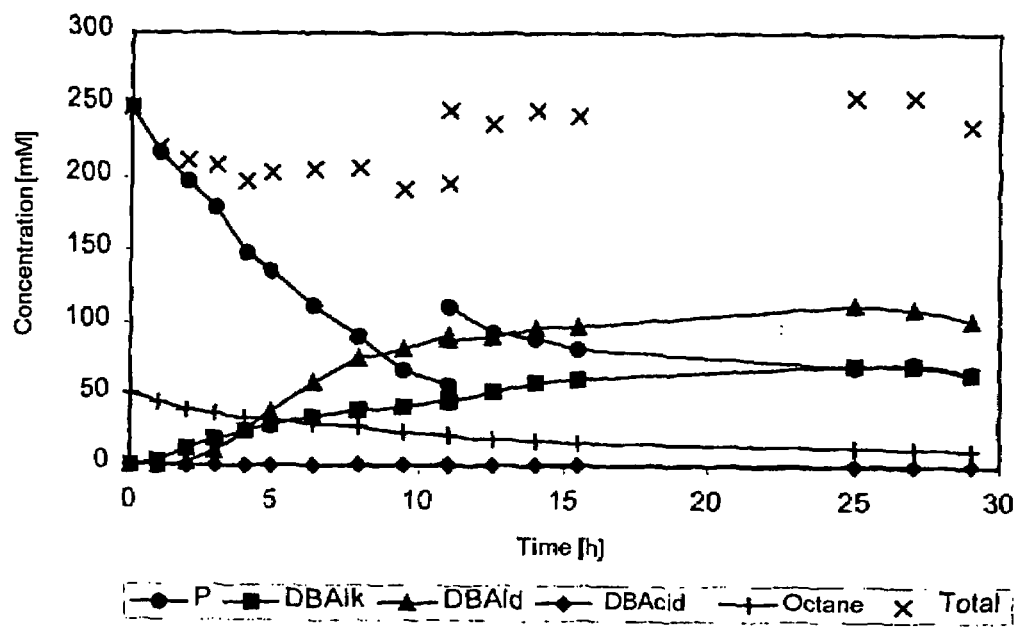

FIG. 9 demonstrates the formation of 3,4-dimethylbenzyl alcohol commenced immediately. The formation of 3,4-dimethylbenzaldehyde commenced after 2 hours. 11 hours after starting the fed-batch culture, another 1% (v/v) of pseudocumene was added. However, only some of this substrate was now converted. The end concentration of 3,4-dimethylbenzylaldehyde was 113 mM. When the biotransformation was stopped, the pseudocumene and 3,4-dimethylbenzyl alcohol concentrations were 65 mM. Virtually no 3,4-dimethylbenzoic acid was produced.

3 hours after the beginning of the fed-batch culture, the cells were fully induced. The specific activity (maximum 13 U/g CDW) and the aldehyde formation rate (maximum 10 U/g CDW) were low. The specific activity dropped steeply 4 hours after the end of the cells' growth period. Following the addition of substrate, an increase to 6 U/g CDW was observed. The aldehyde formation rate too dropped steeply 4 hours after the end of the growth period and remained low.

Starting the fed batch culture with a higher initial cell density did not bring about a higher cell density during the fed batch culture under the chosen conditions. The biomass increased only over 3 hours. A loss in enzyme activity was also observed. A large amount of acetic acid was produced during the fed batch culture.

Experiment 2.3: Fermentation With Normal Cell Density at the Beginning of the Fed Batch Culture It was not possible to achieve a higher cell density in the previous fermentation, despite high cell densities at the beginning of the fed batch culture. Rather, the high initial cell density had negative effects on the biotransformation. Thus, the specific activity was low. Also, the aldehyde formation time observed was short. This is why the fed batch culture was started at a lower cell density.

Figure 10:
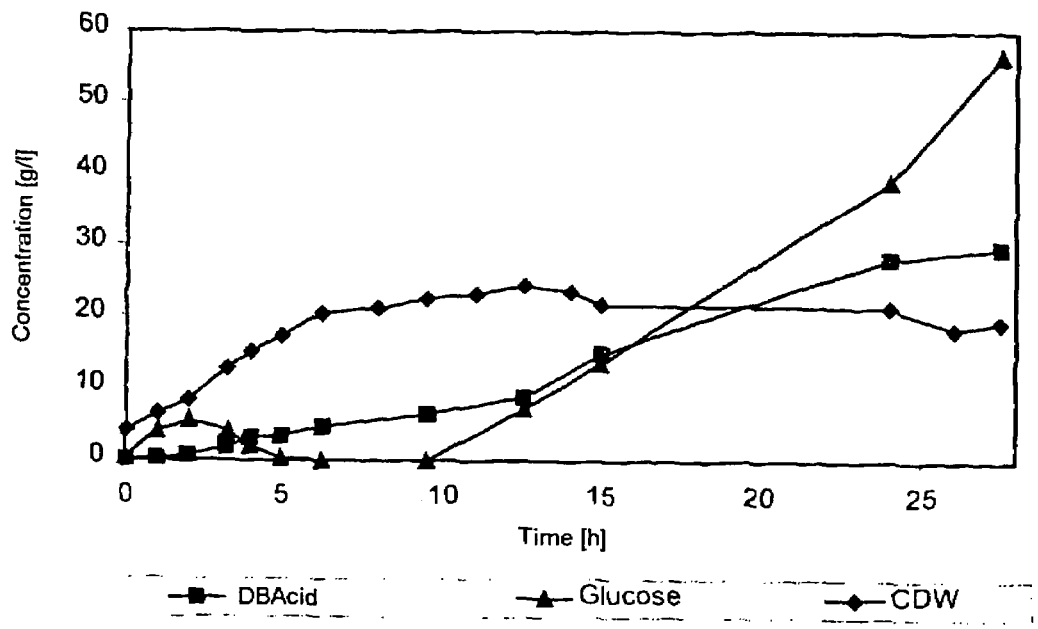

Instead of 2.5% (w/v) of glucose, only 0.7% (w/v) of glucose were added. Starting from a biomass concentration of 4.1 g/l, the cell dry weight at the end of the fed batch culture was 22 g/l. The glucose was fed to the bioreactor at a constant rate of 9 g/h. The acetic acid concentration amounted to approx. 7 g/l after 9 hours. At this point in time, the bacteria had entered the stationary phase (FIG. 10).

Figure 11:
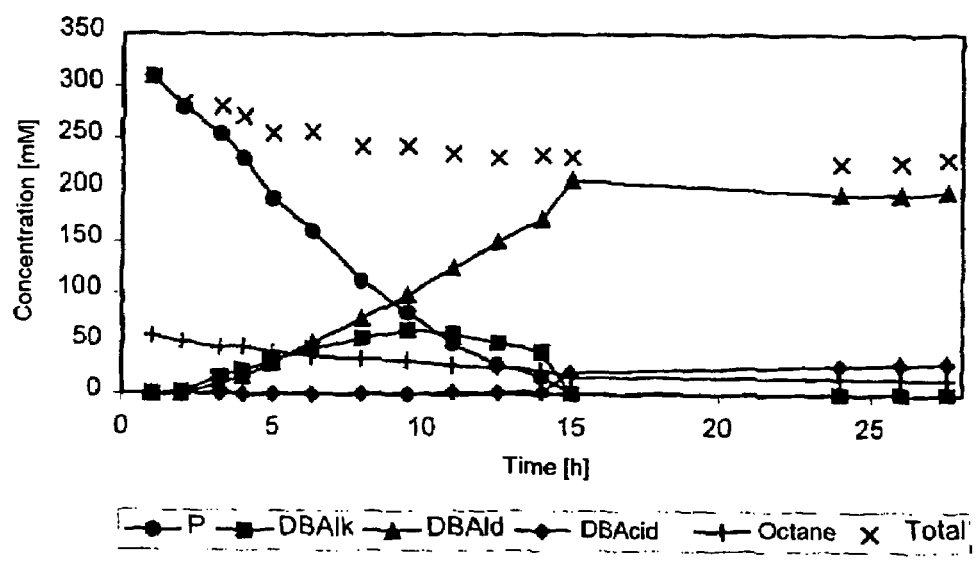

Right at the beginning of the fed batch culture, 0.1% (v/v) of octane was added to the medium. 1 hour later, the organic phase of 4% (v/v) of pseudocumene and 1% (v/v) of n-octane were added. 2 hours after the beginning of the fed batch culture, the cells were fully induced, and 3,4-dimethylbenzyl alcohol and 3,4-dimethylbenzaldehyde started to accumulate in the organic phase. While the alcohol initially accumulated more rapidly than the aldehyde, 3,4-dimethylbenzaldehyde was produced from a substrate concentration of 150 mM. At low pseudocumene concentrations, 3,4-dimethylbenzyl alcohol was converted into 3,4-dimethylbenzaldehyde. The end concentration of 3,4-dimethylbenzaldehyde at the end of the biotransformation amounted to 200 mM. The formation of 3,4-dimethylbenoic acid commenced at low pseudocumene and 3,4-dimethylbenzyl alcohol concentrations (FIG. 11).

3 hours after the beginning of the fed batch culture, the specific activity amounted to 26 U/g CDW. Thereafter, it decreased in parallel with the substrate concentration. After 5 hours, the aldehyde formation rate reached the maximum of 14 U/g CDW. Thereafter, it decreased continuously.

Substrate concentration and initial cell density were chosen optimally to obtain a complete conversion into 3,4-dimethylbenzaldehyde. A lower initial cell density resulted in an aldehyde formation rate for longer.

The Riesenberg medium, which contains no yeast extract in the feed solution, permits the same specific activity and aldehyde formation rate to be achieved as is the case when using the M9 medium only with yeast extract in the feed solution.

Experiment 2.4: Fermentation With Glycerol as Carbon Source

It is possible that the use of glycerol as carbon source has some advantages over glucose as carbon source. Thus, a lower formation of acetic acid and a higher enzyme activity can be expected. This is why the effect of glycerol as carbon source on the biotransformation was studied.

Figure 12:
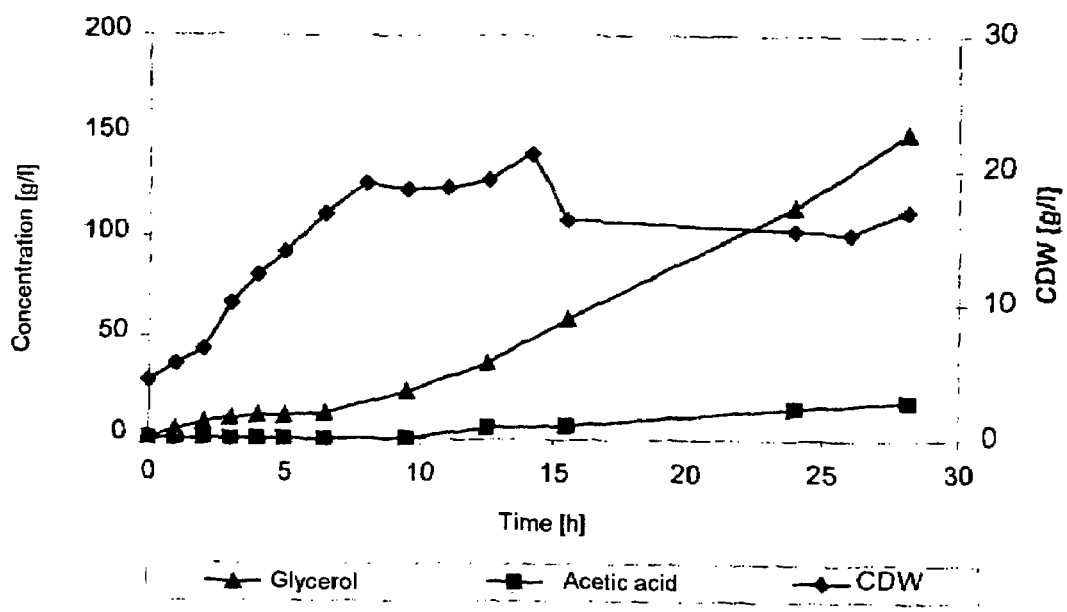

Prior to the inoculation. 0.7% (v/v) of glycerol was added to the medium. At the end of the batch culture, the biomass had a concentration of 4.2 g/l. As expected, a slower biomass growth was observed than when using glucose as carbon source. After the stationary phase had been reached, the cell dry weight was 19 g/l. Right at the beginning of the fed batch-culture, 0.1% (v/v) of octane was added to the medium. After an initial feed rate of 7.7 g/h (glycerol feed rate of 7.2 g/h), the feed rate was increased stepwise to prevent glycerol limitation. The formation of acetic acid commenced only during the stationary phase after 9.5 hours and reached a value of 18 g/l at the end of the fed batch culture (FIG. 12).

Figure 13:
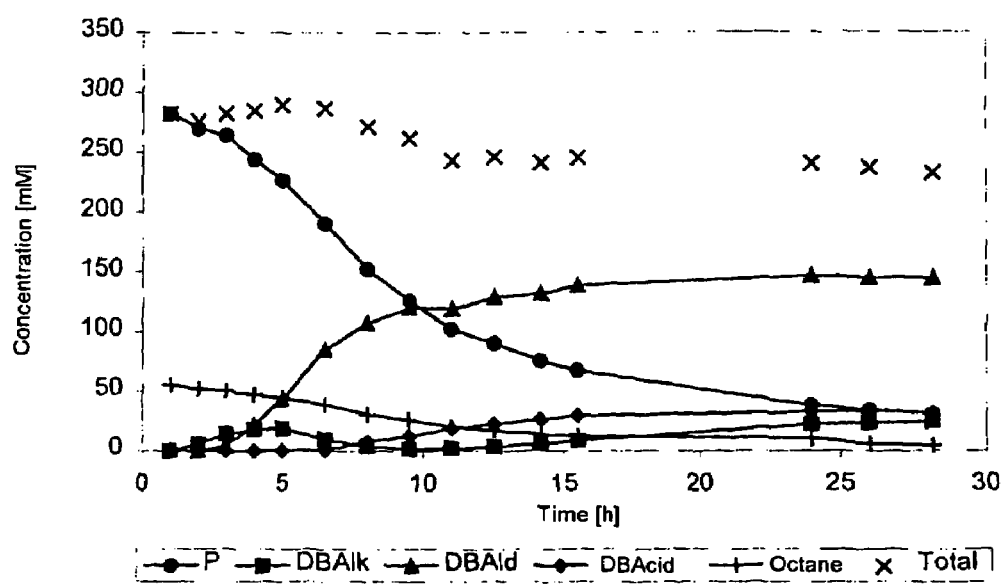

The substrate concentration at the addition of the organic phase amounted to 4% (v/v). 3,4-Dimethylbenzyl alcohol was produced right from the beginning. From a pseudocumene concentration of 240 mM, 3,4-dimethylbenzaldehyde was produced exclusively. 3,4-Dimethylbenzyl alcohol was converted directly into aldehyde. Acid formation commenced at a substrate concentration around 150 mM. As can be seen from FIG. 13, the 3,4-dimethylbenzaldehyde end concentration was 144 mM.

The maximum formation rate of 3,4-dimethylbenzaldehyde was very high (32.7 U/g CDW). The specific overall activity reached a value of 33 U/g CDW. However, the high activities were not maintained for long. After as little as 11 hours, the specific aldehyde formation rate was only 2.5 U/g CDW.

It follows from these results that higher enzyme activities from 30 U/g CDW were achieved when using glycerol as carbon source. However, the activity was only maintained during biomass growth.

Besides the higher enzyme activity, another kinetic was observed in contrast to when glucose was used as carbon source. Thus, 3,4-dimethylbenzaldehyde alone accumulates in the medium at a pseudocumene concentration of as much as 240 mM, in contrast to 150 mM when glucose is used as carbon source. The formation of 3,4-dimethylbenzoic acid too commences at a concentration of as much as 150 mM, which was only the case at 90 mM when glucose was used as carbon source.

Experiment 2.5: Fermentation With Glycerol as Carbon Source and Higher Substrate Concentration In the fermentation as described in Experiment 2.4, it was observed that the accumulation of 3,4-dimethylbenzyl alcohol in the culture liquid stopped at a pseudocumene concentration of as much as 240 mM. It therefore appeared to be possible to start the biotransformation at a higher pseudocumene concentration and to achieve a higher end concentration of 3,4-dimethylbenzaldehyde (DBAld).

Figure 14:
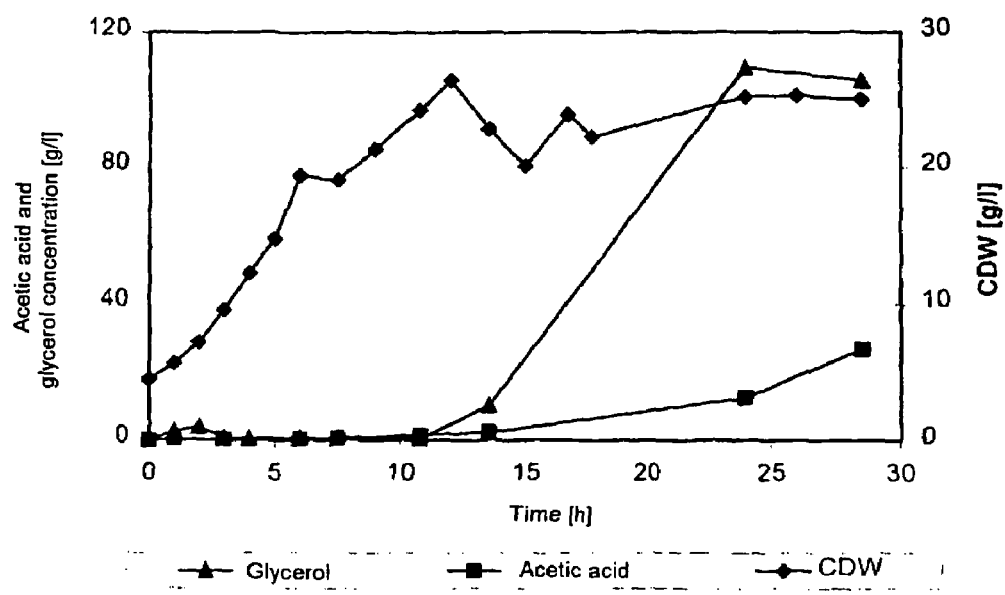

The glycerol concentration at the beginning of the batch culture was 0.7% (v/v). At the beginning, the cell dry weight amounted to 4.4 g/l and reached 25 g/l at the end of the fed batch culture (FIG. 14). At the beginning of the fed batch culture, glycerol was fed in at a rate of 3.7 g/h. Thereafter, the rate was increased stepwise. Up to hour 10, no acetic acid was produced. However, this substance accumulated until the end of the experiment up to a concentration of 26.7 g/l in the medium.

Figure 15:
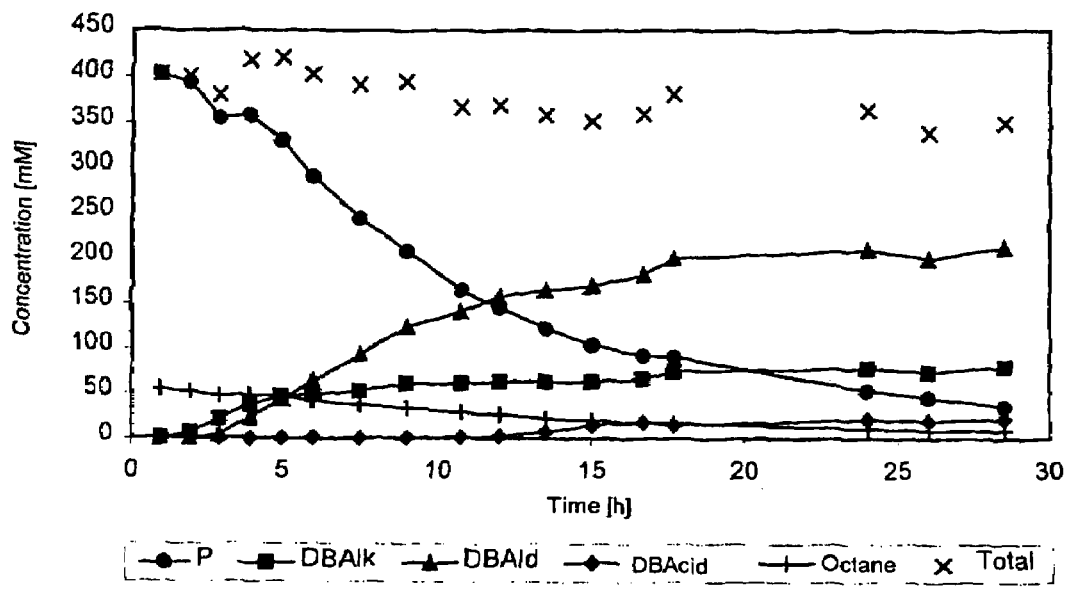

The pseudocumene concentration (in the organic phase) was 5.3% (v/v). At the beginning, the simultaneous formation of 3,4-dimethylbenzyl alcohol (DBAlk) and 3,4-dimethylbenzaldehyde (DBAld) was observed. From a pseudocumene concentration of 300 mM to 150 mM, predominantly DBAld was produced and accumulated. The formation of 3,4-dimethylbenzoic acid (DBAcid) started at a pseudocumene concentration of 150 mM. The end concentration of DBAlk was 80 mM, while the end concentration of DBAld was 212 mM (FIG. 15).

Like in the first fermentation with glycerol, the enzyme activities were high. The specific activity (1 µmol of total product (DBAlk, DBAld and DBAcid) produced per minute/g CDW) reached a value of 46 U/g CDW. The specific formation rate of 3,4-dimethylbenzaldehyde was 22 U/g CDW after 5 hours. In this fermentation too, the activity was only maintained during biomass growth.

The increase in the substrate concentration has no effect on the end concentration of 3,4-dimethylbenzaldehyde since it is not possible to maintain the activity over a prolonged period. The 3,4-dimethylbenzyl alcohol concentration was high at the end of the fed batch culture.

EXAMPLE 3

Repetitive Fed Batch Culture

To monitor the activity of the cells in the absence of kanamycin over a prolonged period, two subsequent fed-batch experiments were carried out, 10 ml of the first fed batch culture acting as inoculum for the second fed batch culture. The purpose was to study the stability of the plasmid and of the XMO genes over several generations without selection pressure. Glucose was used as the carbon source. 4 ml of the thiamine stock solution (1% w/v) and 4 ml of the trace element solution US* were added at the beginning of the feed.

Preculture 1: Inoculate 4 ml of LB medium (1% glucose (w/v), 4 µl kanamycin (50 mg/ml)) with freshly transformed cells and incubate overnight at 37° C.

Preculture 2: Inoculate 100 ml of M9* medium (0.5% glucose (w/v), 200 µl magnesium sulfate, 100 µl trace element solution US*, 100 µl thiamine (1% w/v), 100 µl kanamycin (50 mg/ml)) with 4 ml of preculture 1 and incubate for 10-12 hours at 30° C.

900 ml of medium in the bioreactor are inoculated with 100 ml of preculture. After the batch culture (9-12 h), the fed batch culture is started by continuously feeding a feed solution. 1 hour later, 1 l of organic phase (DOP) comprising the substrate (P) and the inductor (octane) is added to the bioreactor. After 15 hours, the culture liquid is harvested with the exception of a volume of 10 ml, which acts as inoculum for the second fed batch culture. 990 ml of medium are added to the bioreactor. Again, a biotransformation is carried out exactly as described for the $1^{st}$ fed batch culture.

Experiment 3.1: Fed Batch Culture, Day 1

Figure 16:
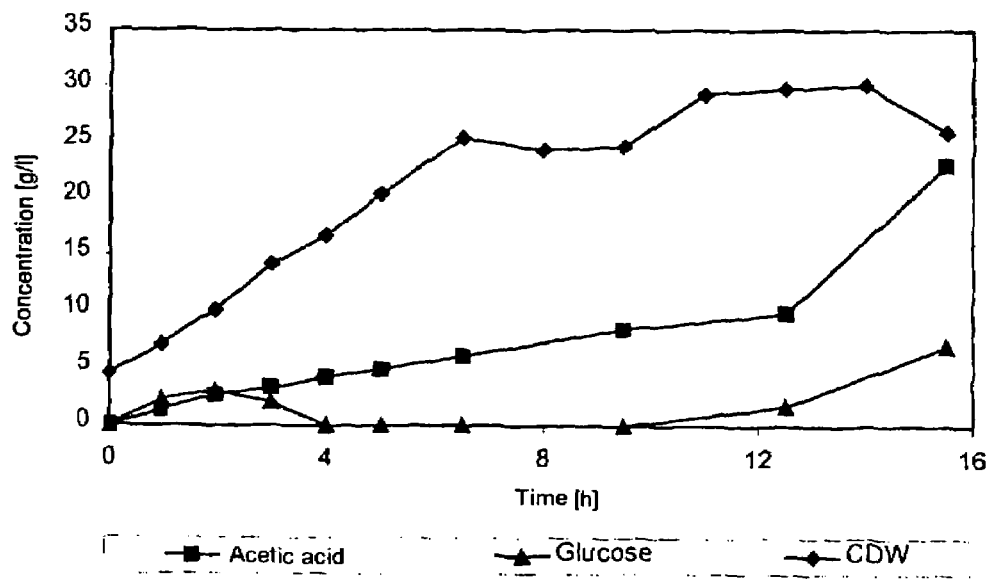

The glucose concentration was 0.7% (w/v) prior to inoculation. At the beginning of the fed batch culture, 0.1% (v/v) of octane was added to the medium in order to induce the cells. Prior to the beginning of the fed batch culture, the biomass amounted to 4.5 g/l; it increased to 28 g/l during the fed batch culture (FIG. 16). The glucose feed rate at the beginning of the fed batch culture was 9 g/h and was subsequently increased stepwise. The acetic acid concentration at the end of the fed batch culture was 25 g/l.

Figure 17:
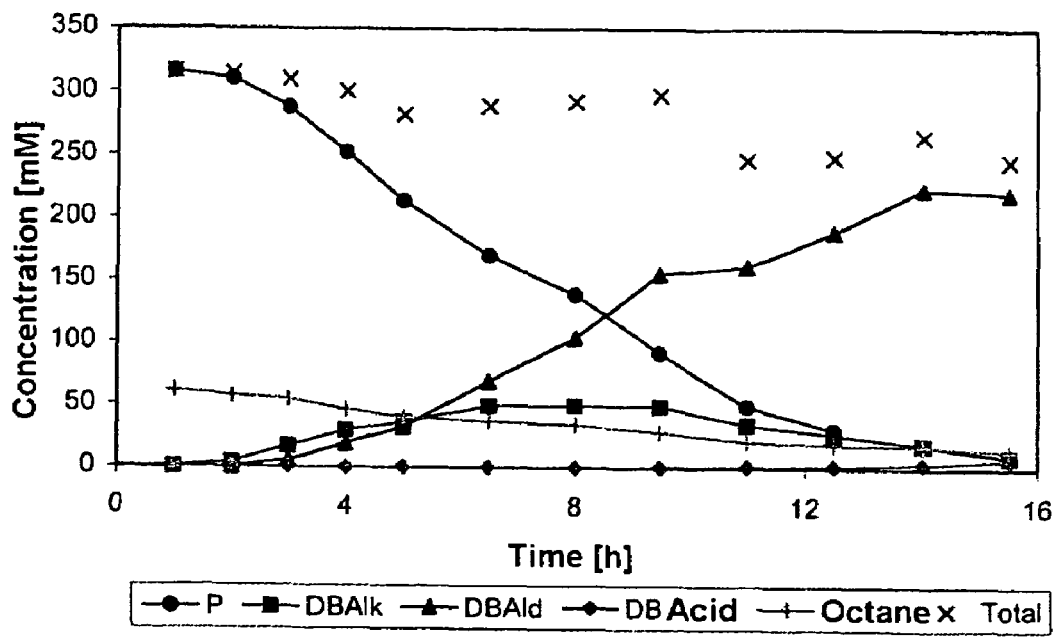
FIG. 17 shows: the concentrations of pseudocumene, 3,4-dimethylbenzyl alcohol, 3,4-dimethylbenzaldehyde, 3,4-dimethylbenzoic acid and octane in the aqueous and organic phase in the repetitive fed-batch culture, day 1

The biotransformation was started at a substrate concentration of 4% (v/v). The course of the pseudocumene, 3,4-dimethylbenzyl alcohol (DBAlk), 3,4-dimethylbenzaldehyde (DBAld), 3,4-dimethylbenzoic acid (DBAcid) and octane concentrations is shown in FIG. 17. First, the formation of 3,4-dimethylbenzaldehyde and 3,4-dimethylbenzyl alcohol was observed. After 6.5 hours after the beginning of the fed batch culture, at a substrate concentration of 150 mM, DBAld was produced predominantly. The formation of acid commenced after 12.5 hours. The 3,4-dimethylbenzaldehyde formation at the end of the biotransformation was 220 mM, and the DBAlk concentration 14 mM. The pseudocumene was utilized during the fed batch culture down to a concentration of 13 mM.

3 hours after the beginning of the fed batch culture, the specific activity was 27 U/g CDW. The aldehyde formation rate reached a maximum of 16 U/g CDW after 5 hours. The enzyme activity was maintained over 15 hours.

Experiment 3.2: Fed Batch Culture, Day 2

Figure 18:
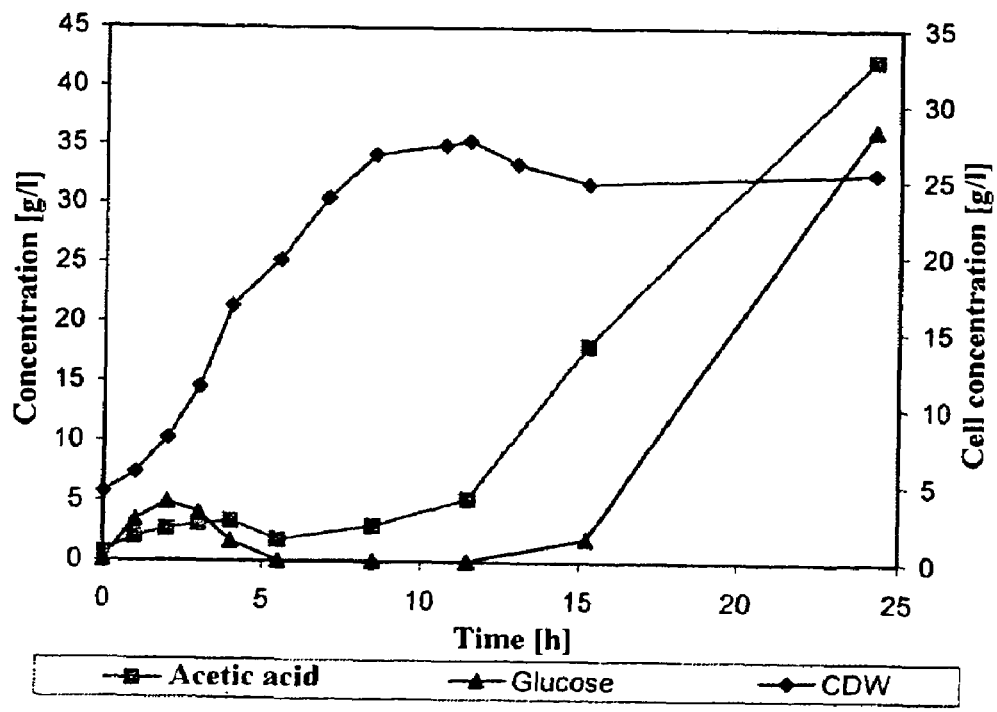
FIG. 18 shows: the cell dry weight, the glucose concentration and the acetic acid concentration in the repetitive fed-batch culture, day 2

Prior to inoculation, the glucose concentration was 0.7% (v/v). After the batch culture, the biomass amounted to 4.5 g/l and reached a concentration of 28 g/l at the end of the fed batch culture. The glucose feed rate at the beginning was 9 g/h, but was increased when glucose limitation was unduly high. The acetic acid concentration at the end of the biotransformation was 44 g/l (FIG. 18).

Figure 19:
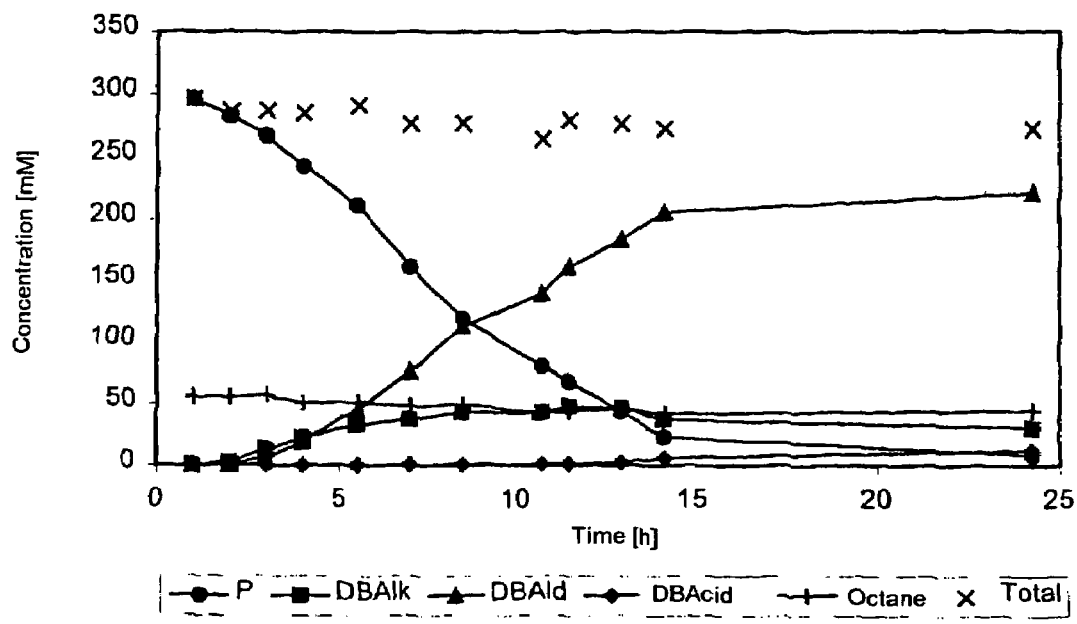
FIG. 19 shows: the concentrations of pseudocumene, 3,4-dimethylbenzyl alcohol, 3,4-dimethylbenzaldehyde, 3,4-dimethylbenzoic acid and octane in the aqueous and organic phase in the repetitive fed-batch culture, day 2

1 hour after the beginning of the fed batch culture, the organic phase, with a substrate concentration of 4% (v/v), was added to the medium. The course of the pseudocumene, DBAld, DBAlk and DBAcid concentrations were similar to the fed batch culture on day 1 (Experiment 3.1). Above a pseudocumene concentration of 150 mM, a simultaneous formation of DBAld and DBAlk was observed. If the substrate concentrations fell short of a value of 150 mM, DBAld was produced predominantly until the end concentration was 220 mM. The formation of DBAcid commenced after 12.5 hours. The DBAlk end concentration amounted to 30 mM and the DBAcid end concentration to 13 mM (FIG. 19).

During the $2^{nd}$ fed batch culture, the specific activity reached an identical maximum (of 27 U/g CDW) as in the fed batch culture of day 1 (Experiment 3.1). Likewise, the aldehyde formation rate reached an identical maximum of 16 U/g CDW. The enzyme activity was maintained over 15 hours.

The two biotransformations gave similar, or indeed identical, results. Thus, high specific activities and aldehyde formation rates were observed in both fed batch cultures. Likewise, identical 3,4-dimethylbenzaldehyde concentrations were obtained at the end of the two biotransformations. In both fed batch cultures, the enzyme activity was maintained over 15 hours. Thus, the plasmid was retained over 60 hours and 14 generations even in the absence of selection pressure.

No significant differences in colonies numbers of the LB agar plates with and without kanamycin were observed.

II. Pilot-Scale Biotransformation Experiments

The biotransformation was carried out on a pilot scale (Examples 4, 5) after the experiments on the laboratory scale had ended. A 42 liter stirred reactor was used for this purpose. The volume of the batch, which consisted of equal parts of Riesenberg medium and organic phase with a substrate concentration of 4.3% (v/v) was 30 liters. 0.7% (w/v) of glucose were added to the medium prior to inoculation. The addition of kanamycin was dispensed with, as was already the case in the repetitive fed batch culture.

EXAMPLE 4

Pilot-Scale Fermentation at pH 6.6

Figure 20:
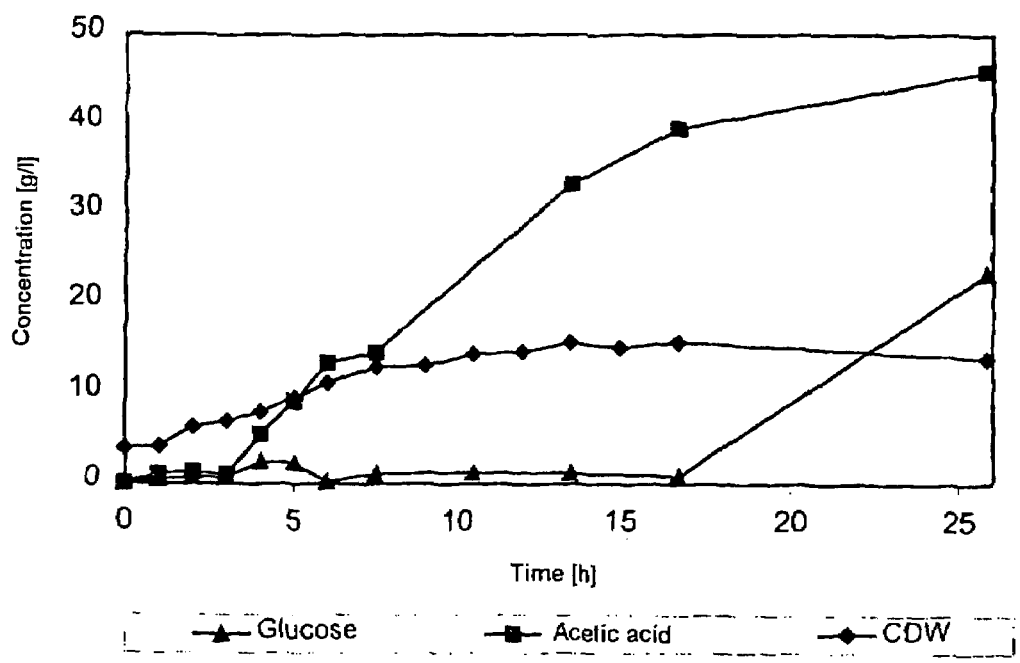
FIG. 20 shows: the cell dry weight, the glucose concentration and the acetic acid concentration in the pilot-scale fermentation at pH 6.6; the arrow indicates the adjustment to pH 6.6

Prior to the beginning of the fed batch culture, the cell dry weight was 4 g/l. However, the end concentration was only 14.5 g/l. 2 hours after induction, the pH was only 6.6 instead of 7.1, owing to a mistake in the pH control. At this point in time, it was observed that cell growth had stopped. The glucose feed rate was 135 g/h (w/v). The cells were not subject to glucose limitation during the biotransformation. The acetic acid concentration increased constantly up to an end concentration of 47 g/l (FIG. 20).

Figure 21:
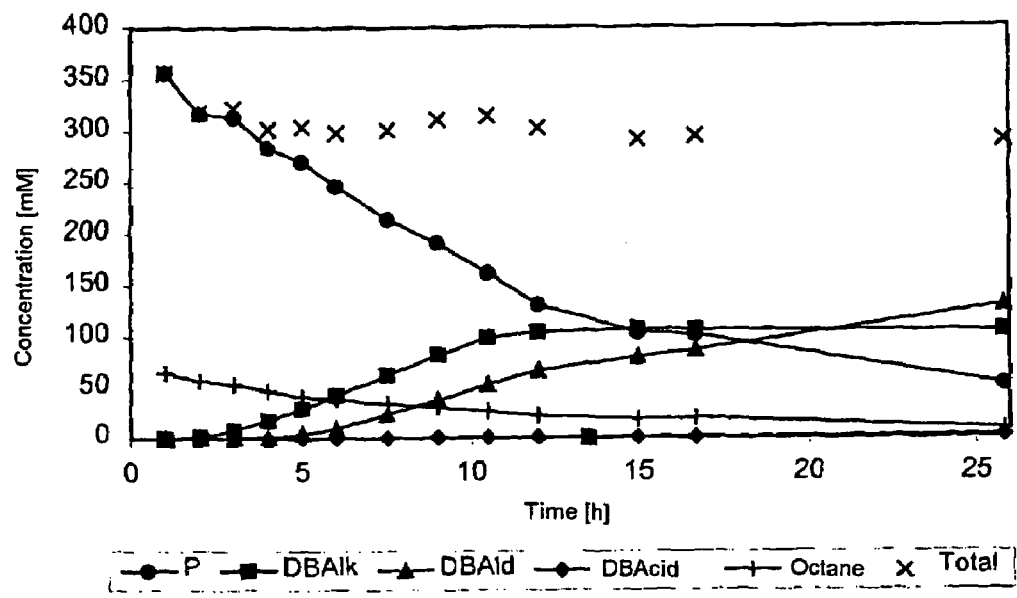
FIG. 21 shows: the concentrations of pseudocumene, 3,4-dimethylbenzyl alcohol, 3,4-dimethylbenzaldehyde, 3,4-dimethylbenzoic acid and octane in the aqueous organic phase in the pilot-scale fermentation

The substrate concentration in the 15 liters of organic phase was 4.3% (v/v). The 3,4-dimethylbenzyl alcohol formation (DBAlk) commenced 2 hours after induction of the cells (FIG. 21). The 3,4-dimethylbenzaldehyde formation commenced only 4 hours after induction of the cells. After 26 hours, the concentration of 3,4-dimethylbenzaldehyde was 130 mM and the concentration of 3,4-dimethylbenzyl alcohol 100 mM. The 3,4-dimethylbenzoic acid formation was very low. Thus, the end concentration amounted to only 2 mM.

The low pH had an effect not only on cell growth but also on enzyme activity. At the beginning of the biotransformation, the specific aldehyde formation rate was low, owing to the pH reduction. However, it recovered after 4 hours at pH 7.1 and reached a value of 12 U/g CDW. The specific total activity reached the maximum of 32 U/g CDW as late as after 7 hours after the beginning of the fed batch culture.

The temporary pH reduction had a powerful effect on biomass growth and enzyme activity. In comparison with preceding fermentations, the biomass reached a low concentration. The volumetric activity (U/l) was accordingly low during the biotransformation.

However, the kinetics of the multi-step process were the same as in the case of the laboratory-scale biotransformations. Thus, 3,4-dimethylbenzyl alcohol was also formed at a pseudocumene concentration of 150 mM.

EXAMPLE 5

Pilot-Scale Fermentation at pH 7.4

Since the preceding fermentation did not yield the expected amount of 3,4-dimethylbenzaldehyde, the experiment was repeated. The pH was increased to 7.4 during the biotransformation, thus, it was also possible to test the effect of an increased pH on the biotransformation.

Figure 22:
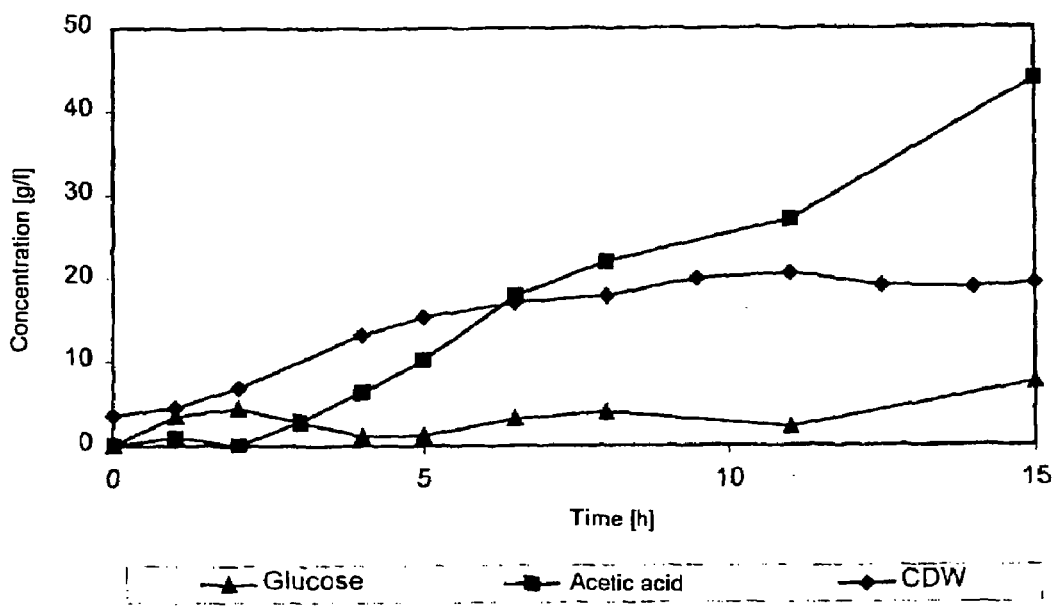
FIG. 22 shows: the cell dry weight, the glucose concentration and the acetic acid concentration in the pilot-scale fermentation at pH 7.4

After the batch culture, the cell dry weight was 3.5 g/l. The cell density increased during the fed batch culture to a value of 20 g/l. Since glucose was never limiting in the medium, the acetic acid concentration in the medium increased continuously (FIG. 22). After the biotransformation, the acetic acid concentration was 45 g/l. As early as one hour after the addition of the organic phase, oxygen was admixed to the air supply to prevent oxygen limitation. Up to hour 6 of biotransformation, the DOT was maintained at a value of between 15% and 25%. Thereafter, the dissolved oxygen content in the medium was between 25% and 40%.

Figure 23:
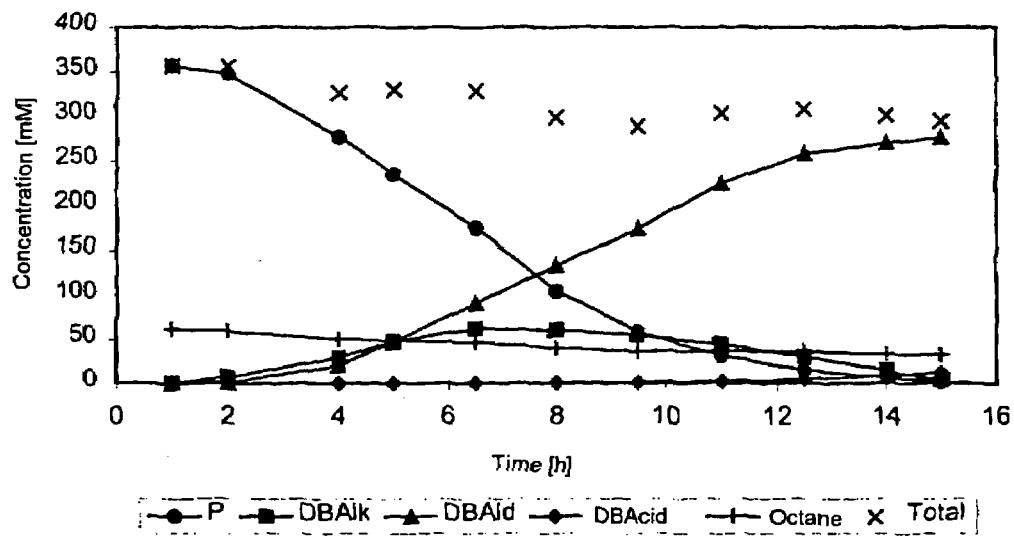
FIG. 23 shows: the concentrations of pseudocumene, 3,4-dimethylbenzyl alcohol, 3,4-dimethylbenzaldehyde, 3,4-dimethylbenzoic acid and octane in the aqueous organic phase in the pilot-scale fermentation at pH 7.4

The course of the pseudocumene, 3,4-dimethylbenzyl alcohol (DBAlk), 3,4-dimethylbenzaldehyde (DBAld) and 3,4-dimethylbenzoic acid (DBAcid) concentrations during biotransformation are comparable to the courses of the laboratory-scale fermentations. At a pseudocumene concentration of 150 mM, mainly 3,4-dimethylbenzaldehyde is accumulated in the culture liquid. Starting from a substrate concentration of 4.8% (v/v), the pseudocumene concentration at the end of the fermentation was 3 mM. The end concentration of DBAlk was 4 mM and the end concentration of DBAcid 12 mM. The 3,4-dimethylbenzoic acid formation commenced after as late as approximately 9 hours. DBAld was produced during the biotransformation up to an end concentration of 275 mM. 78.6% of the substrate added was converted into DBAld (FIG. 23). However, a loss of 16% pseudocumene was recorded during the fed batch culture, owing to the aeration. Thus, when the reactor contents were finally harvested, the percentages shown in Table 3 were present in the organic phase.

TABLE 3

Percentage of pseudocumene, DBAlk, DBAld and DBAcid in the organic phase after the biotransformation

| Substance | [%] in the organic phase |
|---|---|
| Pseudocumene | 1 |
| DBAlk | 1.3 |
| DBAld | 93.6 |
| DBAcid | 4.1 |

Figure 24:
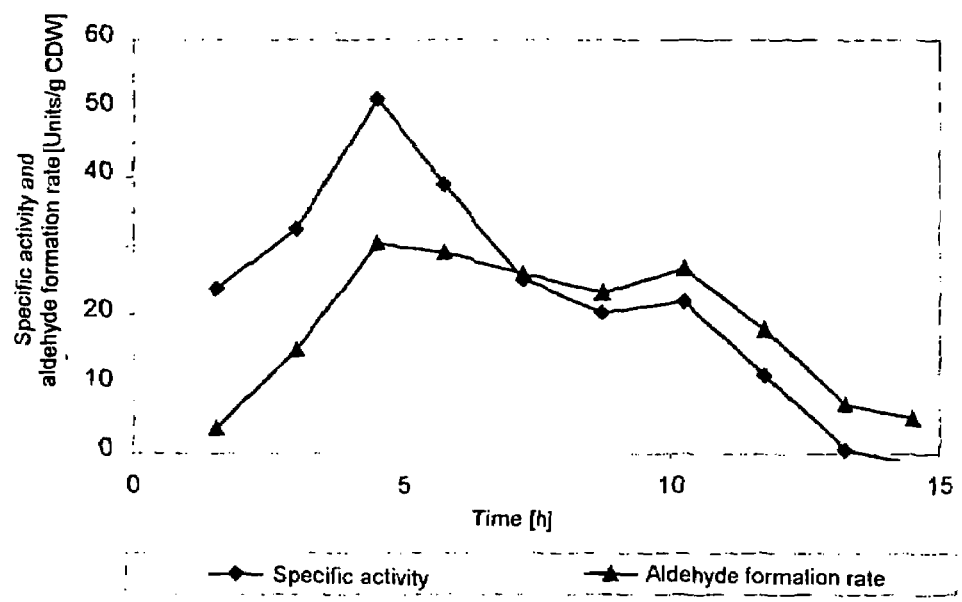
FIG. 24 shows: the specific activity and aldehyde formation rate in the pilot-scale fermentation at pH 7.4; the arrow indicates the increase of the pH to 7.4

The high values of the specific activity (51 U/g CDW) and the aldehyde formation rate (30 U/g CDW) were achieved by increasing the pH from 7.1 to 7.4 three hours after the addition of the organic phase. FIG. 24 is a graphic representation of the courses of the specific total activity and the aldehyde formation rate. Thus, when the pH was increased, a marked increase in the specific activity and the specific aldehyde formation rate were observed after 3 hours.

The substrate added was converted to a high degree into 3,4-dimethylbenzaldehyde, while only small amounts of the by-products 3,4-dimethylbenzyl alcohol and 3,4-dimethylbenzoic acid were formed. Increasing the pH had a positive effect on enzyme activity. Thus, markedly higher specific activity and aldehyde formation rates were achieved after increasing the pH.

The biphasic fed-batch process developed on the laboratory scale was successfully applied to pilot-scale conditions.

EXAMPLE 6

Processing of 3,4-Dimethylbenzaldehyde Obtained in a Pilot-Scale Fermentation at pH 7.4

After the pilot-scale biotransformation had ended, the contents of the bioreactor were harvested. The aqueous phase and the organic phase were separated by centrifugation. The organic phase was subsequently dried by adding sodium sulfate and then separated. Medium-vacuum distillation was employed to separate the 3,4-dimethylbenzaldehyde from the dioctyl phthalate. The vacuum was adjusted between 0.08 mbar and 0.15 mbar. The 3,4-dimethylbenzaldehyde started to distill over at a dioctyl phthalate temperature of 110° C.-120° C.

The distillation gave 484 ml of distillate from 14 liters of dioctyl phthalate. 3,4-Dimethylbenzaldehyde accounted for 96.5% of distillate, 3,4-dimethylbenzyl alcohol for 0.3%, dioctyl phthalate for 2.8%, pseudocumene for 0.3% and octane for 0.04%.

SUMMARY OF THE EXPERIMENTAL RESULTS

1. Optimization of Process-Relevant Parameters

1.1 Effect of Oxygen and Glucose

An important parameter in the production of 3,4-dimethylbenzylaldehyde in a biocatalytic process is the activity of the enzyme. Level and duration of the enzyme activity are of paramount importance.

As has been shown glucose concentration and oxygen supply of the cells have an effect on enzyme activity. Thus, a glucose concentration of above 10 g/l in the medium has an inhibitory effect on enzyme activity. However, an unduly severe glucose limitation also has a negative effect on the productivity of the catalyst.

In this work, it has been demonstrated that simultaneous glucose and oxygen limitation causes xylene monooxygenase to stop catalysis and unspecific *E. coli* alcohol dehydrogenases convert 3,4-dimethylbenzaldehyde back into 3,4-dimethylbenzyl alcohol (FIG. 6).

When oxygen or glucose limitation occurred in isolation and were not unduly severe, no inhibitory effects on activity were observed (FIGS. 16 and 18).

1.2 Effect of Substrate Concentration

Substrate concentration also has an effect on enzyme activity and, at a pseudocumene concentration of below 150 mM in the organic phase, also on the formation of 3,4-dimethylbenzaldehyde. Thus, a low pseudocumene concentration results in low enzyme activity. At a pseudocumene concentration of over 150 mM, only the first step of the multi-step process, the formation of 3,4-dimethylbenzyl alcohol (DBAlk), depends on substrate concentration.

The formation of predominantly 3,4-dimethylbenzaldehyde (DBAld) was observed at a pseudocumene concentration of less than 150 mM. This is why no 3,4-dimethylbenzyl alcohol accumlated in the culture liquid (FIG. 3). For this reason, 3,4-dimethylbenzoic acid (DBAcid) was formed increasingly from a pseudocumene concentration of 90 mM. The formation of 3,4-dimethylbenzyl alcohol, which commenced later, can be attributed to the fact that the enzyme activity was very low at this point in the time.

However, if the initial concentration exceeded 150 mM, the simultaneous accumulation of 3,4-dimethylbenzyl alcohol and 3,4-dimethylbenzaldehyde was observed in the organic phase at the beginning. If the pseudocumene concentration fell to 150 mM, predominantly DBAld was formed. The formation of DBAcid commenced at the end of the biotransformation, when DBAlk was converted virtually quantitively into DBAld (FIGS. 11, 23). This confirms the inhibitory effect on DBAlk on the formation of 3,4-dimethylbenzoic acid.

Even higher initial concentrations of pseudocumene can lead to a pronounced accumulation of 3,4-dimethylbenzyl alcohol in the aqueous phase. If the 3,4-dimethylbenzylalcohol concentration in the aqueous phase exceeds a value of 100 mM, it has a toxic effect on the cells.

1.3 Effect of the Carbon Source

Even though the activities were somewhat higher when using glycerol as carbon source, no more product was formed in the end (FIG. 12 and FIG. 15). Moreover, higher concentrations of by-products accumulated in the organic phase. This can be ascribed inter alia to the shorter duration of activity. Thus, enzyme activity was observed only during biomass growth. When the stationary phase was reached, it was observed that the activity dropped immediately. When using glucose as carbon source, in contrast, enzyme activity was observed well into the stationary-phase. Moreover, it was observed that the 3,4-dimethylbenzyl alcohol formed inhibits the formation of 3,4-dimethylbenzoic acid less when using glycerol as carbon source than was the case with glucose as carbon source (FIG. 15).

1.4 pH Effect

Increasing the pH has a positive effect on enzyme activity. Thus, a marked increase in the specific activity and the aldehyde formation rate was achieved when carrying out the fermentation at a pH of 7.4 instead of 7.1 (FIG. 24). When the pH was set at 7.1 in fermentations, in which glucose was used as carbon source, the maximum aldehyde formation rate was 16 U/g CDW. At pH 7.4, a markedly higher aldehyde formation rate of 30 U/g CDW was achieved. A pH of 6.6 has a markedly negative effect on enzyme activity (productivity).

2. Plasmid Stability 3,4-Dimethylbenzaldehyde is produced in accordance with the invention by recombinant *E. coli* JM101 (pSZP3). Plasmid pSZP3 was developed by Panke (1999). To ensure that the plasmid is retained in the bacteria, it carries a resistance gene which confers resistance to the antibiotic kanamycin. The addition of antibiotic is not desirable in industrial-scale processes for commercial and environmental reasons. This is why experiments were carried out in which the plasmid stability was tested without kanamycin selection pressure. As has been demonstrated by the repetitive batch culture, the plasmid and the XMO genes remain stable over 60 hours. This means that the plasmid is retained and the XMO genes are expressed over 14 generations.

3. Media Optimization

If a biological process is to be exploited industrially, the medium must meet some requirements. Thus, the medium should be as defined as possible. That is to say it should not comprise constituents whose concentrations cannot be determined exactly and which might constitute a risk to product purity. Thus, undefined constituents such as yeast extract or peptone are to be dispensed with if possible.

Obtaining high cell densities in bioprocesses has a pronounced effect on process profitability. Thus, a high-celldensity process may have the following advantages: smaller reactor volume, less complicated preparation and work-up process, and a considerably higher volumetric activity. However, a process involving high cell densities also suffers from problems. High amounts of nutrients must be added, and the oxygen supply of the cells is difficult owing to the high cell density. Moreover, high cell density cultures can be inhibited by metabolic by-products such as ethanol, acetate and lactate which are formed for example under anaerobic conditions. Under aerobic culture conditions too, *E. coli* may form acids and other metabolic by-products, which accumulate in the medium. At a pH of 7, acetic acid has an inhibitory effect on cell growth at a concentration of as little as 5 g/l. This is why an unduly high formation of acid should be prevented in a bioprocess.

Riesenberg (1991) developed a defined medium which does not comprise glucose and magnesium sulfate at the initial stage. It is distinguished by a low formation of acetic acid under unlimited aerobic culture conditions. Using this medium, cell densities of as much as 110 g/l were achieved with *E. coli*. (Riesenberg 1991).

3.1 Effect of Riesenberg Medium

Since, when using M9 medium, cell densities of 20-27 g/l were only achieved with yeast extract in the feed solution, the biotransformation was carried out using Riesenberg medium. As shown in FIG. 8, a high cell density in the batch can be achieved with a suitable glucose concentration. The acetic acid formation was identical to concentrations obtained by Riesenberg, Schulz et al. (1991). Thus, approx. 1 g/l acetic acid was formed. A biotransformation was carried out starting from a cell dry weight of 16 g/l. Despite an abundance of oxygen, a pronounced formation of acetic acid was observed, which finally had an effect on biomass growth. Thus, a cell dry weight of only 24.7 g/l was obtained (FIG. 8). Acetic acid formation was observed even at low glucose concentrations (FIG. 4). This might be attributable to the formation of xylene monooxygenase, which inhibits the growth of *E. coli* (Bühler, Schmid et al. 2000).

When glycerol was used as carbon source instead of glucose, less acetic acid accumulated in the aqueous phase (FIGS. 10 and 12).

The oxygen supply of the cells in a high-cell-density culture is problematic. This is not aided by the fact that the enzyme used for the biotransformation, namely xylene monooxygenase, requires oxygen for catalyzing the substances (Bühler, Schmid et al. 2000). The reactor system was used to full capacity with regard to stirring rate and aeration even with the cell dry weight of less than 30 g/l which was obtained in the fermentations. This is why an oxygen-air mixture had to be used for the aeration on the pilot scale in order to be able to supply the cells with sufficient oxygen.

3.2 Feed Composition

Riesenberg medium is distinguished from M9 medium by its less expensive composition. Moreover, the yeast extract, which causes problems during the process during work-up (foaming, phase separation), was dispensed with in the feed solution.

When yeast extract was dispensed with in the feed solution and the M9 medium was used, adverse effects on biomass growth were observed. Thus, the cell dry weight at the end of the fed batch culture was only 12 g/l (FIG. 4). In contrast, cell densities of 25-30 g/l were achieved with Riesenberg medium. The slower biomass growth rate obtained when using M9 medium might be attributable to the lower ammonium concentration in comparison with Riesenberg medium.

4. Combined Effect of Various Parameters

Figure 25:
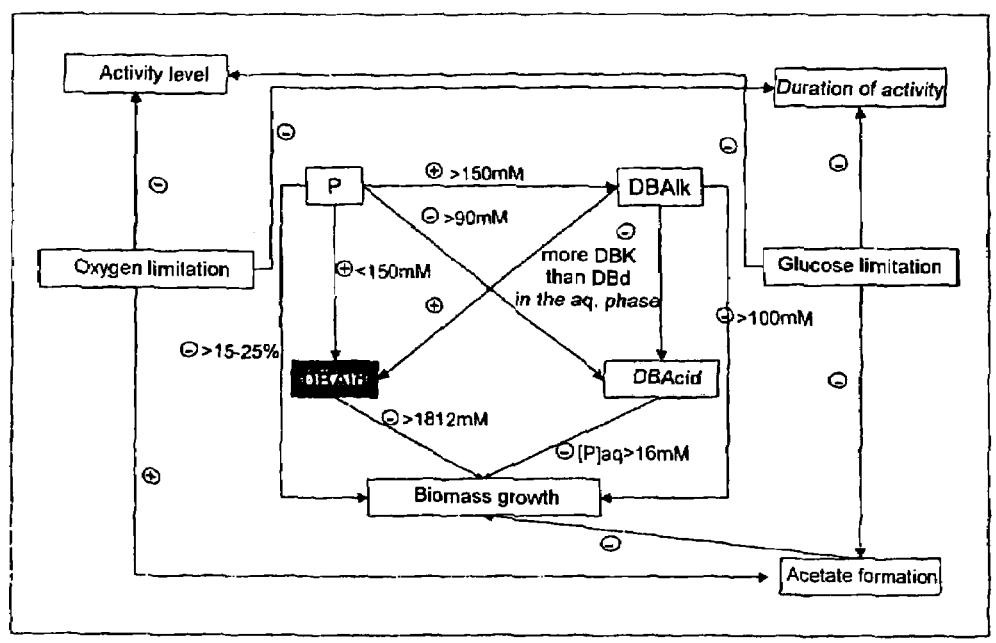
FIG. 25 shows: the effects of process-relevant parameters on the bioprocess P: pseudocumene, DBAlk: 3,4-dimethylbenzyl alcohol, DBAld: 3,4-dimethylbenzaldehyde, DBA: 3,4-Dimethylbenzoic acid +enhancing effect; −inhibitory effect

Process-relevant parameters were determined and improved within the invention. FIG. 25 is a schematic representation of the various parameters and their effects on the overall process.

As already described, the dissolved oxygen and the glucose concentration in the medium have a substantial effect on level and duration of activity. Substrate and product concentrations have a toxic effect on the biomass, depending on the substance. Thus, DBAcid inhibits biomass growth at a concentration of as little as 16 mM in the aqueous phase. The DBAlk concentration, which inhibits biomass growth, is at a concentration of 100 mM in the aqueous phase and the DBAld concentration 1812 mM. If the pseudocumene concentration exceeds 15-25% in the aqueous phase, it is also toxic to the cells. Likewise, the acetic acid concentration has an inhibitory effect on biomass growth.

5. Isolation of the Product 5.1 Phase Separation

The first step after the reactor contents have been harvested is phase separation by centrifugation. As already mentioned, it was found that the addition of yeast extract and glycerol to the medium had adverse effects on the separation process. Thus, an intermediate phase which accounted for up to a third of the volume to be separated has formed. A comparable effect was observed when the stirring rate exceeded 2000 rpm. This phenomenon can be attributed to proteins present in the yeast extract or to destruction of the cells owing to an unduly high stirring rate.

5.2 Distillation 3,4-Dimethylbenzaldehyde is a substance with a high boiling point. The boiling point at atmospheric pressure is 220-223° C. The organic phase dioctyl phthalate, which is used in accordance with the invention, has a boiling point of 380° C. This large difference in the boiling points of the two substances made it possible to purify 3,4-dimethylbenzaldehyde by distillation.

To remove the 3,4-dimethylbenzaldehyde from the organic phase by distillation, the solution would have to be heated to substantially beyond 223° C. This is why medium-vacuum distillation appeared the method of choice.

6. Pilot-Scale Biotransformation

As has been demonstrated in accordance with the invention, the biphasic fed batch process developed for the production of 3,4-dimethylbenzaldehyde can be scaled up without major problems. After optimization of the process-relevant parameters and the medium on a laboratory scale, the process was applied to the pilot scale. The only aspect which proved to be a problem during the biotransformation was the oxygen supply of the cells. Thus, oxygen had to be admixed to the air supply as early as 2 hours after induction of the cells.

REFERENCES

F. Ausubel et al.,(1997) Current Protocols in Molecular Biology, Wiley Interscience, New York Bühler, B., A. Schmid, et al. (2000). "Xylene monooxygenase catalyzes the multistep oxygenation of toluene and pseudocumene to corresponding alcohols, aldehydes, and acids in *Escherichia coli* JM101." *The Journal of Biological Chemistry* 275(14): 10085-10092.

Harayama, S., M. Kok, et al. (1992). "Functional and evolutionary relationships among diverse oxygenases." *Ann. Rev. Microbiol.* 46: 565-601.

Harayama, S., R. A. Leppik, et al. (1986). "Gene order of the TOL catabolic plasmid upper pathway operon and oxidation of both toluene and benzyl alcohol by the xylA product." *Journal of Bacteriology* 167(2): 455-461.

Harayama, S., M. Rekik, et al. (1989). "Characterization of five genes in the upper-pathway operon of TOL plasmid pWW0 from *Pseudomonas putida* and identification of the gene products." *Journal of Bacteriology* 171(9): 5048-5055.

Legoy, M. D., H. S. Kim, et al. (1985). "Use of alcohol dehydrogenase for flavor aldehyde production." *Process Biochemistry* 20: 145-148.

Molinari, F., F. Aragozzini, et al. (1997). "Continuous production of isovaleraldehyde through extractive bioconversion in a hollow-fiber membrane bioreactor." *Enzyme and Microbial Technology* 20: 604-611.

Molinari, F., R. Gandolfi, et al. (1999). "Biotransformations in two-liquid-phase systems. Production of phenylacetaldehyde by oxidation of 2-phenylethanol with acetic acid bacteria." *Enzyme and Microbial Technology* 25: 729-735.

Molinari, F., R. Villa, et al. (1995). "Aldehyde production by alcohol oxidation with Gluconobacter oxydans." *Applied Microbiology and Biotechnology* 43: 989-994.

Panke, S. (1999). Production of (S)-styrene oxide with recombinant bacteria. *Institute of Biotechnolgy*. Zurich, Swiss Federal Institute of Technology: 208.

Pouwels P. H. et al, (1985) "Cloning Vectors", eds., Elsevier, Amsterdam-N.Y.-Oxford Ramos, J. L., S. Marqués, et al. (1997). "Transcriptional control of the *Pseudomonas* TOL plasmid catabolic operons is achieved through an interplay of host factors and plasmid-encoded regulators." *Annual Reviews in Microbiology* 51: 341-373.

Riesenberg, D. (1991). "High-cell-density cultivation of *Escherichia coli.*" *Current Opinion in Biotechnology* 2: 380-384.

Sambrook, J., E. F. Fritsch, et al. (1989). *Molecular cloning: a laboratory manual, 2nd ed.* Cold Spring Harbor, N.Y., Cold Spring Harbor Laboratory.

Schmid, A. (1997). Der Metabolismus von ortho-Hydroxybiphenylen in *Pseudomonas azeleica* HBP1, Universitat Stuttgart.

Simmonds, J. and G. K. Robinson (1997). "Novel biotransformations to produce aromatic and heterocyclic aldehydes." *Enzyme and Microbial Technology* 21: 367-374.

Simmonds, J. and G. K. Robinson (1998). "Formation of benzaldehyde by *Pseudomonas putida* ATCC 12633." *Applied Microbiology and Biotechnology* 50: 353-358.

Williams, P. A., L. M. Shaw, et al. (1997). "xylUW, two genes at the start of the upper pathway operon of TOL plasmid pWWO, appear to play no essential part in determining its catabolic potential." *Microbiology* 143: 101-107.

Wittcoff, H. A. and B. G. Reuben (1996). *Industrial Organic Chemicals.* New-York, John Wiley & Sons. Inc.

We claim:

1. A process for the biocatalytic oxidation of aromatic compounds in an oxidation reaction, which comprises:

growing, under aerobic conditions, a microorganism that expresses an enzyme with xylene monooxygenase (XMO) activity in a biphase aqueous-organic reaction medium, said medium containing an aqueous phase and an organic phase, and further containing an aromatic substrate of the formula II $$Ar—R^2 \qquad (II)$$

in which Ar is an unsubstituted or mono- or polysubstituted mononuclear aromatic ring, and $R^2$ is —$(CH_2)_{n+1}R^3$ where n is an integer from 0 to 15; and $R^3$ is H or OH.

2. The process of claim 1, wherein the microorganism that expresses XMO activity has essentially no benzaldehyde dehydrogenase (BZDH) activity.

3. The process of claim 1, wherein the organic phase contains a polar organic compound with a partition coefficient of greater than $10^4$ in a biphasic n-octanol/water system.

4. The process as claimed in claim 1, wherein the organic phase contains a phthalate.

5. The process of claim 4, wherein the phthalate is selected from the group consisting of a di($C_5$-$C_{12}$-alkyl) phthalate, a dioctyl phthalate, phthalates that act as antifoams, a plurality of different phthalates, and combinations thereof.

6. The process of claim 1, wherein the enzyme with XMO activity is selected from the group consisting of XMO enzymes, isoenzymes of XMO enzymes, functional equivalents of XMO enzymes, XMO enzymes derived from *Pseudomonas*, XMO enzymes derived from *Pseudomonas putida* strain mt-2, and combinations thereof.

7. The process of claim 1, wherein the microorganism that expresses XMO activity has essentially no benzyl alcohol dehydrogenase (BADH) activity.

8. The process of claim 1, wherein the microorganism is a recombinant microorganism transformed with an expression vector containing XMO-encoding genes xylM and xylA.

9. The process of claim 8, wherein the recombinant microorganism is transformed with expression plasmid pSPZ3.

10. The process of claim 1, wherein the microorganism is a bacterium from the genus *Escherichia*.

11. The process of claim 1, wherein enzyme expression is commenced by adding an inductor to the reaction medium.

12. The process of claim 1, wherein the reaction medium contains essentially no antibiotic.

13. The process of claim 1, wherein the reaction medium contains essentially no antibiotic.

14. The process of claim 8, wherein the XMO-encoding genes xylM and xylA are operably linked with a regulatory alk system from *Pseudomonas* oleovorans GPo 1.

15. The process of claim 1, wherein the oxidation reaction further contains a pseudocumene.

16. The process of claim 1, wherein the oxidation reaction is carried out as a semicontinuous batch operation.

17. The process of claim 1, further comprising isolating a product from the reaction medium.

18. The process of claim 17, wherein the organic phase is separated prior to isolation of said product.

19. The process of claim 18, wherein the product is isolated by distillation of the separated organic phase.

20. The process of claim 17, wherein the organic phase has a boiling point at 1 atm that exceeds the boiling point of the product by approximately 50 to 200° C.

21. The process of claim 17, wherein productivity of product isolation is determined by a process parameter.

22. The process of claim 21, wherein the process parameter is selected from the group consisting of aeration of the reaction medium, oxygen input to the reaction medium, concentration of one or more starting materials in the reaction medium, pH of the reaction medium, composition of the reaction medium, feed time of the microorganism in the reaction medium, feed rate of the microorganism in the reaction medium, and combinations thereof.

23. The process of claim 17, wherein the product has the formula Ia $$Ar\!-\!(CH_2)_n\!-\!R^1 \qquad (Ia)$$

wherein $R^1$ is CHO or COOH.

24. The process of claim 23, wherein $R^1$ is CHO.

25. The process of claim 23, wherein $R^1$ is COOH.

26. The process of claim 17, wherein the product has the formula Ib $$Ar\!-\!(CH_2)_{n+1}OH \qquad (Ib).$$

* * * * *

UNITED STATES PATENT AND TRADEMARK OFFICE
CERTIFICATE OF CORRECTION

| | | |
|---|---|---|
| PATENT NO. | : 7,368,267 B2 | Page 1 of 1 |
| APPLICATION NO. | : 10/473973 | |
| DATED | : May 6, 2008 | |
| INVENTOR(S) | : Andreas Schmid et al. | |

It is certified that error appears in the above-identified patent and that said Letters Patent is hereby corrected as shown below:

In Claim 12, column 34, "The process of claim 1, wherein the reaction medium contains essentially no antibiotic" should read -- The process of claim 1, wherein the microorganism expresses a *Pseudomonas putida* mt-2 xylene monooxygenase --.

Signed and Sealed this

Fifteenth Day of July, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,368,267 B2 | Page 1 of 1 |
| APPLICATION NO. | : 10/473973 | |
| DATED | : May 6, 2008 | |
| INVENTOR(S) | : Andreas Schmid et al. | |

It is certified that error appears in the above-identified patent and that said Letters Patent is hereby corrected as shown below:

In Claim 12, column 34, lines 46 and 47, "The process of claim 1, wherein the reaction medium contains essentially no antibiotic" should read -- The process of claim 1, wherein the microorganism expresses a *Pseudomonas putida* mt-2 xylene monooxygenase --.

This certificate supersedes the Certificate of Correction issued July 15, 2008.

Signed and Sealed this

Fifth Day of August, 2008

JON W. DUDAS
*Director of the United States Patent and Trademark Office*